US008388958B2

(12) United States Patent
Comoglio et al.

(10) Patent No.: US 8,388,958 B2
(45) Date of Patent: Mar. 5, 2013

(54) ANTI-*MET* MONOCLONAL ANTIBODY, FRAGMENTS AND VECTORS THEREOF, FOR THE TREATMENT OF TUMORS AND CORRESPONDING PRODUCTS

(75) Inventors: Paolo Maria Comoglio, Candiolo (IT); Elisa Vigna, Candiolo (IT); Silvia Giordano, Candiolo (IT)

(73) Assignee: Metheresis Translational Research SA, Lugano (CH)

( * ) Notice: Subject to any disclaimer, the term of this patent is extended or adjusted under 35 U.S.C. 154(b) by 894 days.

(21) Appl. No.: 12/223,623

(22) PCT Filed: Feb. 5, 2007

(86) PCT No.: PCT/EP2007/051066
§ 371 (c)(1),
(2), (4) Date: Oct. 1, 2008

(87) PCT Pub. No.: WO2007/090807
PCT Pub. Date: Aug. 16, 2007

(65) Prior Publication Data
US 2009/0285807 A1 Nov. 19, 2009

(30) Foreign Application Priority Data

Feb. 6, 2006 (EP) ..................................... 06101345

(51) Int. Cl.
*A61K 39/00* (2006.01)
(52) U.S. Cl. ................ 424/133.1; 424/130.1; 424/138.1; 424/143.1
(58) Field of Classification Search .......................... None
See application file for complete search history.

(56) References Cited

U.S. PATENT DOCUMENTS 6,214,344 B1    4/2001  Schwall et al.

FOREIGN PATENT DOCUMENTS

WO          2005/016382        2/2005

OTHER PUBLICATIONS

[Fundamental Immunology p. 242 (William E. Paul, M.D. ed., 3d ed; 1993)].*
International Search Report for PCT/EP2007/051066 mailed May 21, 2007.
Written Opinion for PCT/EP2007/051066 mailed May 21, 2007.
Petrelli et al., "Ab-induced ectodomain shedding mediates hepatocytes growth factor receptor down-regulation and hampers biological activity", *Proceedings of the National Academy of Sciences*, vol. 103, No. 3, Mar. 2006, pp. 5090-5095, XP002389316.
Cortesina et al., "Staging of head and neck squamous cell carcinoma using the MET oncogene product as marker of tumor cells in lymph node metastases", *International Journal of Cancer*, vol. 89, No. 3, May 2000, pp. 286-292, XP002430067.
Bardelli et al., "Agonist Met antibodies define the signaling threshold required for a full mitogenic and invasive program of Kaposi's Sacoma cells", *Biochemical and Biophysical Research Communications*, vol. 334, No. 4, Sep. 2005, pp. 1172-1179, XP005001511.
Prat et al., "Agnostic Monoclonal Antibodies Against the Met Receptor Dissect the Biological Responses to HGF", *Journal of Cell Science*, vol. 111, No. 2, 1998, pp. 237-247, XP000943567.
Hay et al., "Nuclear imaging of Met-expressing human and canine cancer xenografts with radiolabeled monoclonal antibodies", *Clinical Cancer Research*, vol. 11, No. 19, pt. 2, Oct. 2005, pp. 7064s-7069s, XP002430068.
Micieli et al, "Targeting the tumor and its microenvironment by a dual-function decoy Met receptor", *Cancer Cell*, vol. 6, No. 1, Jul. 2004, pp. 61-73, XP002389313.
Wajih et al., "Vascular origin of a soluble truncated form of the hepatocyte growth factor receptor (c-met)", *Circulation Research*, vol. 90, No. 1, Jan. 2002, pp. 46-52, XP0238914.
Galvani et al., "Suramin modulates cellular levels of hepatocyte growth factor receptor by inducing shedding of a soluble form", *Biochemical Pharmacology*, vol. 50, No. 7, 1995, pp. 959-966, XP002389315.
Balyasnikova et al., "Epitope-specific antibody-induced cleavage of angiotensin-converting enzyme from the cell surface", *Biochemical Journal*, vol. 362, No. 3, Mar. 2002, pp. 585-595, XP002389317.
Amendola et al., "Coordinate dual-gene transgenesis by lentiviral vectors carrying synthetic bidirectional promoters", *Nature Biotechnology*, vol. 23, No. 1, Jan. 2005, pp. 108-116, XP002389318.
First Office Action (with English translation) dated Apr. 10, 2012 issued in connection with corresponding Japanese Application No. 2008-553739.
Cortesina et al, "Staging of Head and Neck Squamous Cell Carcinoma Using the *MET* Oncogene Product As Marker of Tumor Cells in Lymph Node Metastases", Int. J. Cancer (Pred. Oncol.) 89 (3):286-292 (2000).
The Japanese Society of Gastroenterological Surgery 32(6):1394 (1999).

* cited by examiner

*Primary Examiner* — Brad Duffy
(74) *Attorney, Agent, or Firm* — Nixon & Vanderhye P.C.

(57) ABSTRACT

Use of a monoclonal antibody directed against the extracellular domain of hepatocyte growth factor is disclosed for the preparation of a medicament for the treatment of tumors and/or metastases and of a diagnostic tool for detecting neoplastic cells as well as vectors comprising at least a portion of the nucleotide sequence encoding the anti-Met monoclonal antibody, products containing the anti-Met monoclonal antibody and/or at least one fragment thereof and at least one kinase inhibitor.

13 Claims, 17 Drawing Sheets

Fig. 1
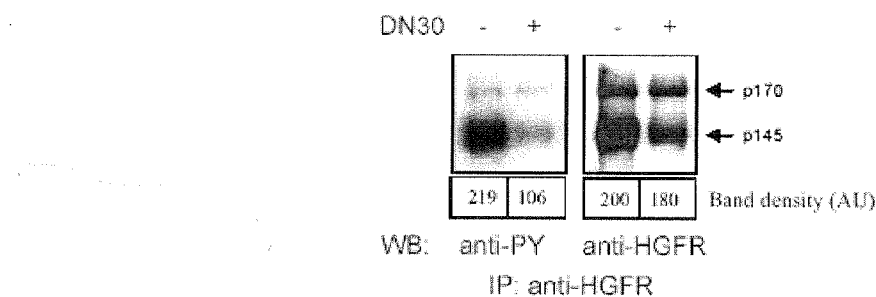
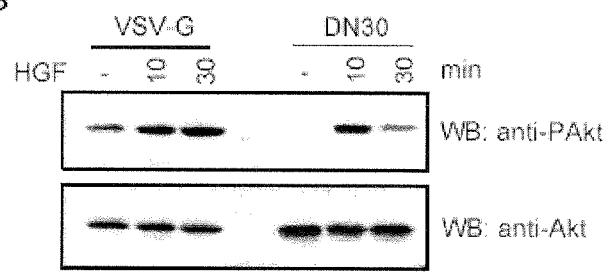
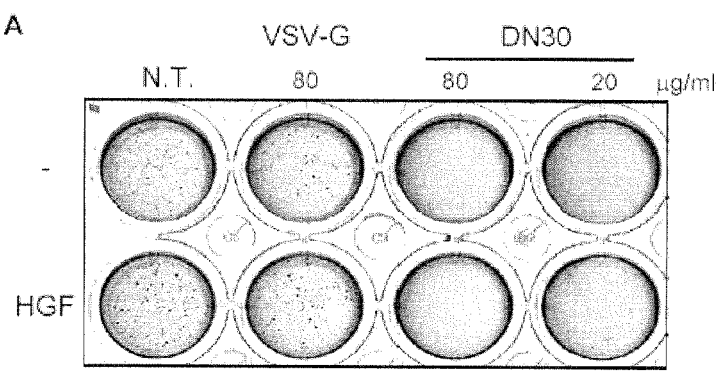
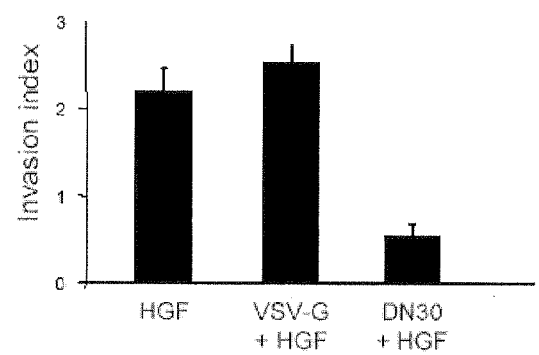
Fig. 2

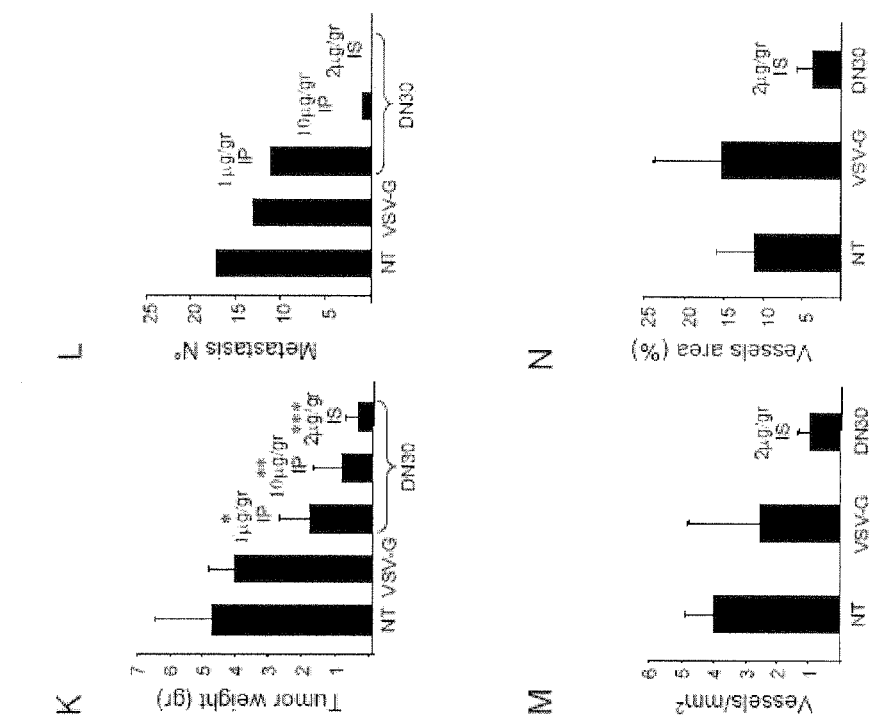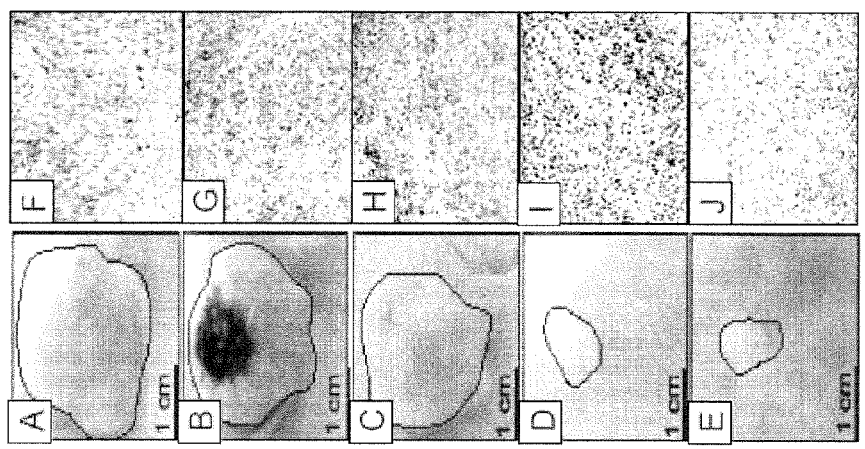
Fig. 4

Fig. 6
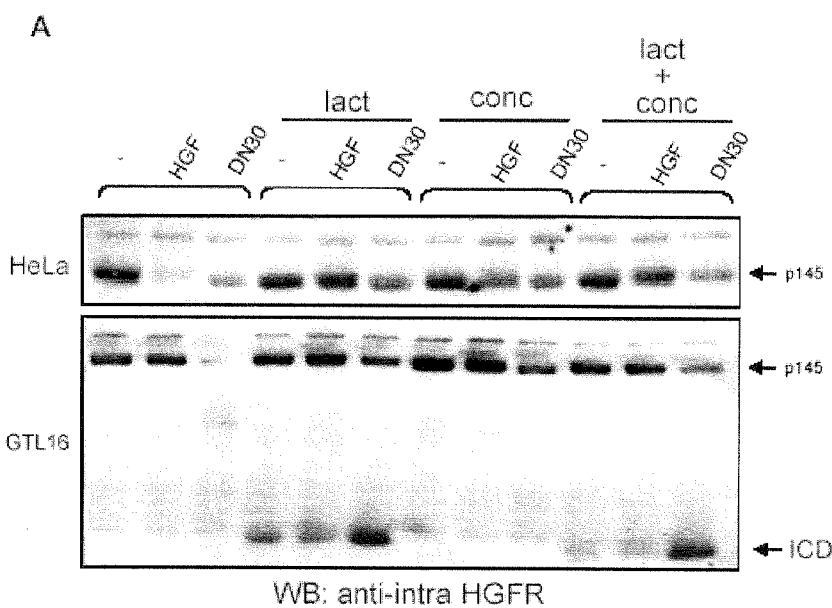
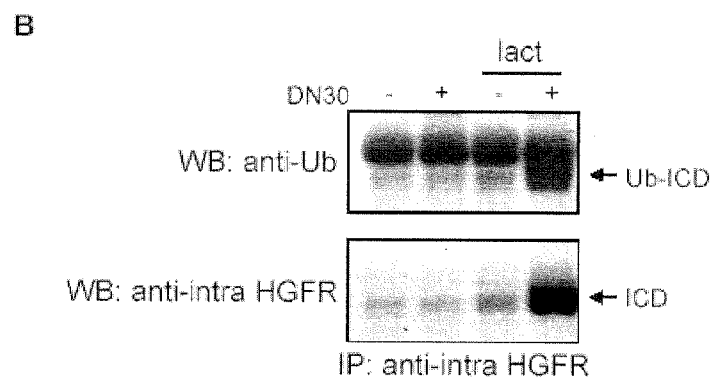

Fig. 20
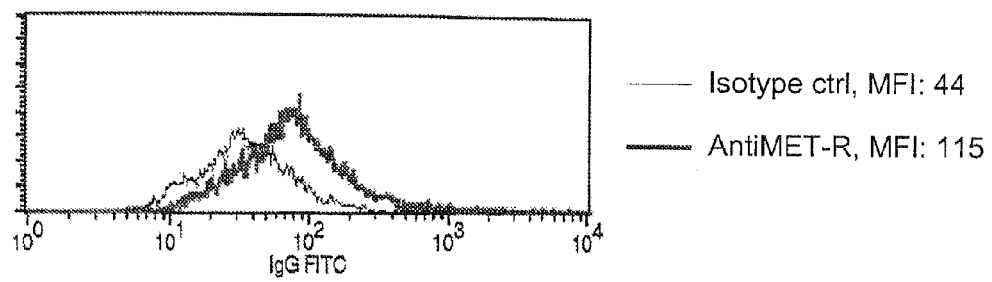
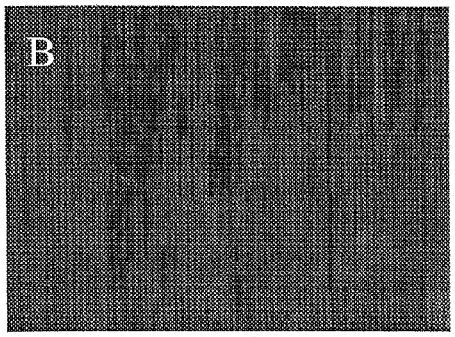
Ctrl
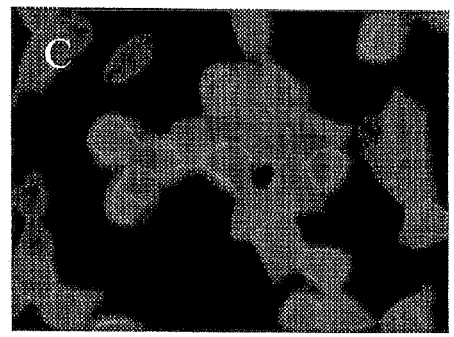
AntiMET-R

Figure 21a

```
atgggatgga gctatatcat cctcttttg gtagcaacag ctacagatgg ccactcccag    60
gtccaactgc agcagcctgg gactgaactg tgaagcctg ggcttcagt gaagctgtcc    120
tgcaaggctt ctggctacac cttcaccagt tactggatac actgggtgaa gcagaggcct    180
ggacaaggcc ttgagtggat tggagagatt aatcctagca gcggtcgtac taactacaac    240
gagaaattca agaacaaggt cacagtgact gtagacaaat cttccaccac agcctacatg    300
caactcagca acctgacatc tgaggactct gcggtctatt actgtgcaag tagggctac    360
tggggccaag gcaccactct cacagtctcc tcagccaaaa caacagccc atcggtctat    420
ccactggccc ctgtgtgtgg aaatacaact ggctcctcgg tgactctagg atgcctggtc    480
aagggttatt ccctgagcc agtgaccttg acctggaact ctggatccct gtccagtggt    540
gtgcacacct tcccagctgt cctgcagtct gacctctaca ccctcagcag ctcagtgact    600
gtaacctcga gcacctggcc cagccagtcc atcacctgca atgtggccca ccggcaagc    660
agcaccaagg tggacaagaa aattgagccc agagggccca caatcaagcc ctgtcctcca    720
tgcaaatgcc cagcacctaa cctcttgggt ggaccatccg tcttcatctt ccctccaaag    780
atcaaggatg tactcatgat ctccctgagc cccatagtca catgtgtggt ggtggatgtg    840
agcgaggatg acccagatgt ccagatcagc tggtttgtga acaacgtgga agtacacaca    900
gctcagacac aaacccatag agaggattac aacagtactc tccgggtggt cagtgccctc    960
cccatccagc accaggactg gatgagtggc aaggagttca atgcaaggt caacaacaaa    1020
gacctcccag cgcccatcga gagaaccatc tcaaaaccca agggtcagt aagagctcca    1080
caggtatatg tcttgcctcc accagaagaa gagatgacta agaaacaggt cactctgacc    1140
tgcatggtca cagacttcat gcctgaagac atttacgtgg agtggaccaa caacgggaaa    1200
acagagctaa actacaagaa cactgaacca gtcctggact ctgatggttc ttacttcatg    1260
tacagcaagc tgagagtgga aaagaagaac tgggtggaaa gaaatagcta ctcctgttca    1320
gtggtccacg agggtctgca caatcaccac acgactaaga gcttctcccg gactccgggt    1380
aaatga                                                              1386
```

Figure 21b

MGWSYIILFLVATATDGHSQVQLQQPGTELVKPGASVKLSCKASGYTFTSYWIHWVKQRPGQGLEW
IGEINPSSGRTNYNEKFKNKVTVTVDKSSTTAYMQLSNLTSEDSAVYYCASRGYWGQGTTLTVSSA
KTTAPSVYPLAPVCGNTTGSSVTLGCLVKGYFPEPVTLTWNSGSLSSGVHTFPAVLQSDLYTLSSS
VTVTSSTWPSQSITCNVAHPASSTKVDKKIEPRGPTIKPCPPCKCPAPNLLGGPSVFIFPPKIKDV
LMISLSPIVTCVVVDVSEDDPDVQISWFVNNVEVHTAQTQTHREDYNSTLRVVSALPIQHQDWMSG
KEFKCKVNNKDLPAPIERTISKPKGSVRAPQVYVLPPPEEEMTKKQVTLTCMVTDFMPEDIYVEWT
NNGKTELNYKNTEPVLDSDGSYFMYSKLRVEKKNWVERNSYSCSVVHEGLHNHHTTKSFSRTPGK

Figure 22a

```
atggagacag acacaatcct gctatgggtg ctgctgctct gggttccagg ctccactggt    60
gacattgtgc tgacccaatc tccagcttct ttggctgtgt ctctagggca gagggccacc   120
atctcctgca aggccagcca aagtgttgat tatgatggtg gtagttatat gagttggttc   180
caacagagac caggacagcc acccaaactc ctcatctctg ctgcatccaa tctagaatct   240
gggatcccag ccaggtttag tggcagtggc tctgggacag acttcaccct caatatccat   300
cctgtggagg aggaggatgt tgcaacctat tactgtcagc aaagttatga ggatccgctc   360
acgttcggtg ctgggaccaa gctggagctg aaacgggctg atgctgcacc aactgtatcc   420
atcttcccac catccagtga gcagttaaca tctggaggtg cctcagtcgt gtgcttcttg   480
aacaacttct acccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc   660
actcacaaga catctacttc acccattgtc aagagcttca caggaatga gtgttag     717
```

Figure 22b

```
METDTILLWVLLLWVPGSTGDIVLTQSPASLAVSLGQRATISCKASQSVDYDGGSYMSWFQQRPGQ
PPKLLISAASNLESGIPARFSGSGSGTDFTLNIHPVEEEDVATYYCQQSYEDPLTFGAGTKLELKR
ADAAPTVSIFPPSSEQLTSGGASVVCFLNNFYPKDINVKWKIDGSERQNGVLNSWTDQDSKDSTYS
MSSTLTLTKDEYERHNSYTCEATHKTSTSPIVKSFNRNEC
```

ANTI-*MET* MONOCLONAL ANTIBODY, FRAGMENTS AND VECTORS THEREOF, FOR THE TREATMENT OF TUMORS AND CORRESPONDING PRODUCTS

This application is the U.S. national phase of International Application No. PCT/EP2007/051066, filed 5 Feb. 2007 which designated the U.S. and claims the benefit to European Patent Application No. 06101345.4, filed 6 Feb. 2006, the entire contents of each of which are hereby incorporated by reference.

FIELD OF THE INVENTION

The present invention concerns the use of a monoclonal antibody, fragments and/or portions thereof, and the use of the nucleotide sequence coding for a monoclonal antibody, fragments and/or portions thereof for the preparation of a medicament for the treatment of tumors and metastases and diagnostic devices to detect neoplastic cells, either in vivo, or in vitro. In particular, the present invention concerns the use of an anti-Met monoclonal antibody directed against the extracellular domain of hepatocyte growth factor receptor.

BACKGROUND OF INVENTION

Scientific exploration of cancer immunotherapy began in the 1950s and the first application relied on polyclonal antibodies. Today, after more than five decades, immunotherapy with monoclonal antibodies continues to offer a promising alternative for cancer treatment (1,2). Several antibodies targeting tyrosine kinase receptors (RTKs) in cancer are currently used in clinical practice (3). The mechanism of action of these antibodies is different in different instances, and—in spite of examples of successful application—often, is poorly understood (4). Bevacizumab and Cetuximab target VEGF-VEGFR and EGF-EGFR, respectively, and act by preventing ligand-receptor interaction, (5,6). Herceptin is a monoclonal antibody specific for HER2, a member of the EGFR family. The mechanism of action underlying Herceptin efficacy is not completely clear but it has been shown that it promotes HER2 degradation, thus decreasing receptor levels at the surface of tumor cells (7).

The MET oncogene, encoding the tyrosine kinase receptor for Hepatocyte Growth Factor (HGF), controls genetic programs leading to cell growth, invasion and protection from apoptosis. Deregulated activation of HGFR is critical not only for the acquisition of tumorigenic properties but also for the achievement of the invasive phenotype (8). The role of MET in human tumors emerged from several experimental approaches and was unequivocally proved by the discovery of MET activating mutations in inherited forms of carcinomas. (9,10). Moreover, HGFR constitutive activation is frequent also in sporadic cancers and studies from this and other laboratories have shown that the MET oncogene is overexpressed in tumors of specific histotypes or is activated through autocrine mechanisms. Besides, the MET gene is amplified in hematogenous metastases of colorectal carcinomas (11). Interfering with Met activation is thus becoming a challenging approach to hamper the tumorigenic and metastatic processes. In the past years, several strategies have been proposed to block aberrant HGFR signalling, targeting either the HGFR itself or its ligand. These approaches include the use of HGF antagonists, HGF neutralizing antibodies, HGFR decoys, small molecule ATP binding site inhibitors of HGFR or small molecules such as geldanamycin, SH2 domain polypeptides and ribozymes (reviewed in 12).

SUMMARY OF THE INVENTION

The present invention is related to the use of a monoclonal antibody directed against the extracellular domain of Hepatocyte Growth Factor Receptor (HGFR) in the treatment of tumors and/or metastases in a subject affected by a tumor and in diagnostic devices to detect neoplastic cells, either in vivo, or in vitro.

Object of the present invention is, thus, the use of i) an anti-Met monoclonal antibody, ii) a fragment containing the epitope binding region of an anti-Met monoclonal antibody and/or iii) a genetically engineered antibody containing the epitope binding region or the complementarity determining regions (CDRs) of an anti-Met monoclonal antibody for the preparation of a medicament for the treatment of tumors and metastases in a subject suffering from a tumor and for diagnostic devices to detect neoplastic cells, either in vivo, or in vitro, wherein the anti-Met monoclonal antibody—named AntiMET-R—is produced by the hybridoma cell line deposited by Advanced Biotechnology Center (ABC), Interlab Cell Line Collection (ICLC), S.S. Banca Cellule e Colture in GMP, Largo Rosanna Benzi 10, Genova, Italy with accession number ICLC PD 05006. The deposit was made Dec. 29, 2005.

Another object of the present invention is the use of a vector comprising at least a portion of the nucleotide sequence encoding for the epitope binding region or the CDRs of the anti-Met monoclonal antibody produced by the hybridoma cell line ICLC PD 05006 for the preparation of a medicament for the treatment of tumors and metastases in a subject affected by a tumor.

Another object of the present invention is the use of i) the anti-Met monoclonal antibody, ii) a fragment containing the epitope binding region of the anti-Met monoclonal antibody and/or iii) a genetically engineered antibody containing the epitope binding region or the CDRs of the anti-Met monoclonal antibody and at least one kinase inhibitor as a combined preparation for simultaneous, separate or sequential use in tumor and/or metastases therapy.

Another object of the present invention is a method for screening compounds able to bind to at least one portion of the extra cellular domain of Hepatocyte Growth Factor Receptor (HGFR) for the identification of compounds pharmacologically active in the prevention and/or treatment of tumor and/or metastases.

Another object of the present invention is the use of the AntiMET-R antibody, fragments thereof and/or genetically engineered antibodies containing the epitope binding region or the CRDs of the AntiMET-R antibody as diagnostic tool to detect neoplastic cells, either in vivo, or in vitro.

According to the present invention, these purposes are achieved by means of the claims that follow, which are integral part of the technical teaching herein provided with respect to the invention.

BRIEF DESCRIPTION OF THE DRAWINGS

FIG. 1. AntiMET-R impairs HGFR activation and signal transduction (A) Evaluation of HGFR activation. GTL16 cells were exposed to AntiMET-R for the indicated times. HGFR was immunoprecipitated from cell lysates and Western blots were probed with the indicated Abs. AntiMET-R treatment resulted in a decrease of receptor activation more pronounced than receptor down-regulation, as indicated by band density quantification. (B) Analysis of HGFR signalling. Cells were pre-treated either with VSV-G or AntiMET-R and then stimulated with HGF for the indicated times. Akt phosphorylation was evaluated in cell total lysates. As shown in the upper panel, AntiMET-R reduced both basal and HGF-induced Akt activation.

FIG. 2. AntiMET-R inhibits the transformed phenotype of cancer cells in vitro. (A) Anchorage-independent growth of GTL16 cells. Pre-treated cells were seeded in 0.5% agar. Cells were then maintained in the presence of the indicated amounts of AntiMET-R or VSV-G Abs and after 10 days, grown colonies were stained. Anchorage-independent growth was drastically inhibited even at low doses of AntiMET-R. (B) Invasion assay. MDA-MB-435 β4 were pre-treated with the indicated antibodies for 24 hrs prior to seeding on a matrigel-coated Transwell chamber. The lower chamber was filled with DMEM 2% FBS+100 ng/ml HGF. After 24 hrs, migrated cells were stained and counted. Invasive capacity in response to HGF is expressed as fold increase compared to not stimulated cells. As shown, AntiMET-R treatment significantly reduced cell invasion.

Immunoistochemical analysis of tumors relieved that the levels of activated HGFR were strongly decreased in mice treated with AntiMET-R.

FIG. 4. AntiMET-R treatment interferes with tumor progression in vivo. Nude mice were inoculated subcutaneously with $2.5 \times 10^6$ MDA-MB-435 β4 cells. Tumor growth was evaluated in untreated mice (A) and in mice treated with: 10 μg/gr VSV-G administered IP (B), 1 μg/gr AntiMET-R IP (C), 10 μg/gr AntiMET-R IP (D) and 2 μg/gr AntiMET-R IS (E). As shown in the diagram (K), AntiMET-R inhibited tumor growth in nude mice engrafted with human tumor cells. Immunohistochemical staining for anti human phospho-HGFR was carried out on sections of tumor shown in the left panel. Strong HGFR activation was present both in untreated mice (F) and in mice treated with control antibody (G). Administration of AntiMET-R resulted in HGFR inhibition that paralleled with impairment of tumor growth (H-J). (L) Analysis of pulmonary metastases. Metastases were counted by microscopical observation of the lung sections after hematoxylin/eosin staining. A dose-dependent reduction of metastases number was evident in AntiMET-R treated mice. (M-N) Evaluation of tumor vascularisation. Immunofluorescence staining on tumor histological sections was performed with an anti-mouse CD31 antibody. Number and area of vessels were evaluated by fluorescence microscopy. As shown, both the number and the size of vessels were reduced in response to AntiMET-R treatment.

Figure 5:
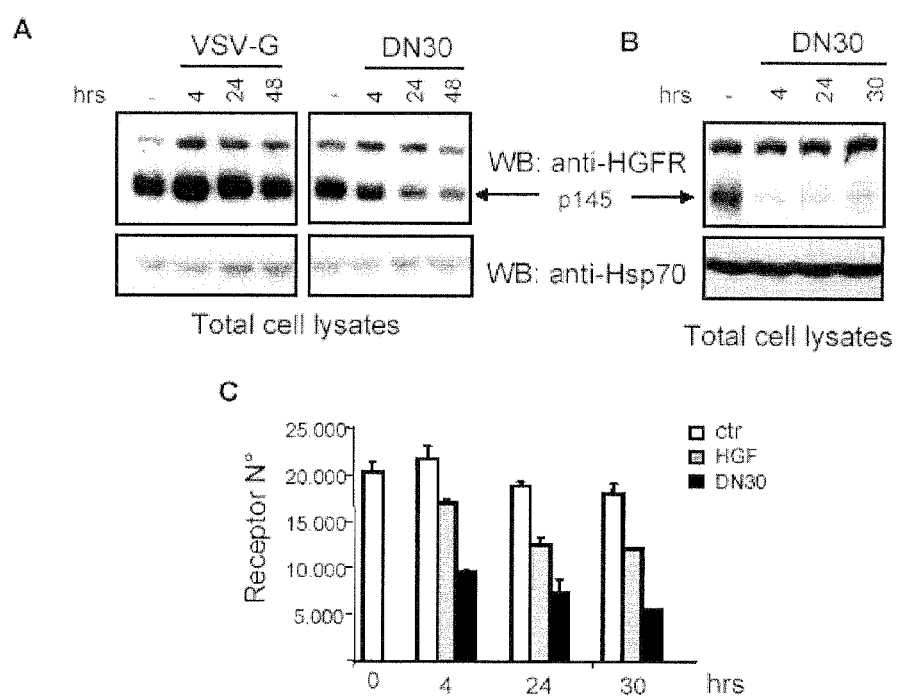

FIG. 5. AntiMET-R induces HGFR down-regulation. GTL16 cells (A) and MDA-MB-435 β4 (B) were treated with AntiMET-R for the indicated times. Equal amounts of total cell lysates were processed for Western blotting and probed with anti-HGFR (upper panels) or, as a loading control, with anti-Hsp70 (lower panels) antibodies. As shown, AntiMET-R was able to induce HGFR down-regulation both in over-expressing cells (GTL16) and in cells expressing normal levels of HGFR (MDA-MB-435 β4). (C) Cytofluorimetric quantification of HGFR on the cell surface. MDA-MB-435 β4 cells were incubated in medium alone (black bars) or HGF (grey bars) or AntiMET-R (white bars). At the indicated time points, cells were stained with an anti-extra HGFR Ab (DO24). As shown, AntiMET-R was able to efficiently reduce the amount of surface HGFR with the maximal reduction after 30 hrs of treatment.

FIG. 6. Antibody-induced and ligand-dependent down-regulation follows different pathways. (A) HeLa (upper panel) and GTL16 (lower panel) cells were pre-treated with either lactacystine (lact) or concanamycin (conc) or both for 2 hours, before treatment with HGF or AntiMET-R. HGFR down-regulation was evaluated on total cell lysates. In the presence of proteasome inhibitors, ligand-induced HGFR down-regulation was impaired, while Ab-induced was not. In this condition, a 60 Kd fragment (arrow), detectable only by an Ab directed against the intracellular portion (anti-intra Met), was accumulated in cells. Moreover, probing with anti-ubiquitin antibodies (B, upper panel) showed that this fragment was tagged with ubiquitin moieties, as expected for a molecule committed to proteasomal degradation.

Figure 7:
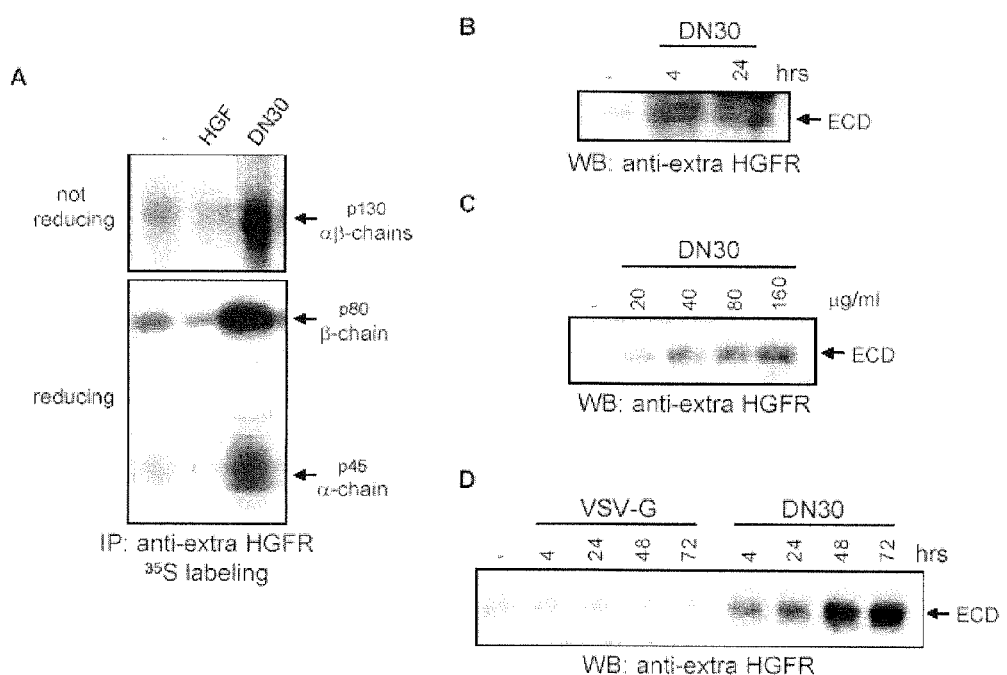

FIG. 7. AntiMET-R induces the proteolytic cleavage of HGFR and shedding of the Extra-Cellular Domain (ECTODOMAIN). (A) GTL16 cells were metabolically labelled with $^{35}$S Methionine and $^{35}$S Cysteine and then treated with either HGF or AntiMET-R for 4 hrs. Supernatants were collected and immunoprecipitated with anti-HGFR Ab directed against the extracellular domain. Gels were run under non-reducing (upper panel) or reducing (lower panel) conditions. In the absence of reducing agents HGFR α and β chains migrate as a complex, while the two bands run separately in the presence of β-mercapto ethanol. As shown in the figure, AntiMET-R but not HGF was able to induce shedding of HGFR ectodomain. (B) AntiMET-R induces ectodomain shedding also in endothelial cells. HUVEC cells were exposed to the antibody for the indicated times. Culture media were collected and immunoprecipitated with an antibody recognizing the extracellular portion of HGFR β-chain. Western blots were probed with the same anti-extra HGFR. (C,D) HGFR shedding is dose- and time-dependent. Cells were stimulated with increasing amount of AntiMET-R(C) or for different times (D) Culture media were treated as in (B)

Figure 8:
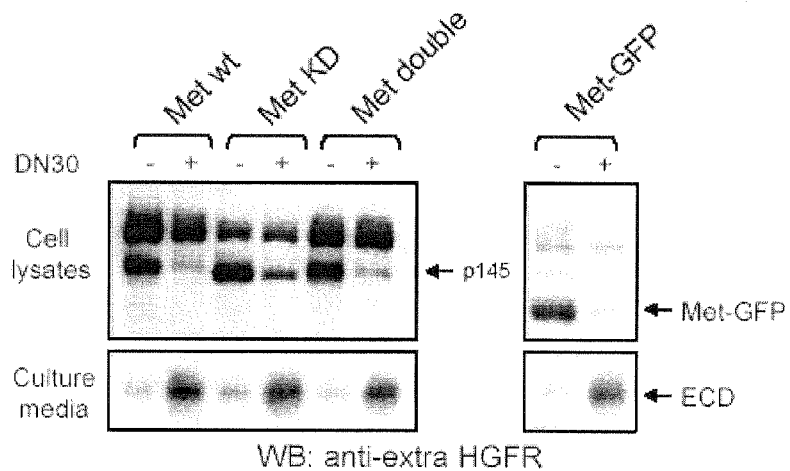

FIG. 8. Activation of signal transduction is not required for HGFR shedding. Cos-7 cells were transfected with different HGFR mutants and 48 hours later were treated with Anti-MET-R for 4 hrs. Equal amount of total cell lysates and conditioned media were processed for Western blotting. As shown, AntiMET-R was able to induce down-regulation and ectodomain shedding of all HGFR mutants. HGFR KD=HGFR Kinase Dead, lacking kinase activity; HGFR Double=HGFR mutant lacking the 2 docking tyrosines 1349, 1356 and thus unable to recruit signal transducers; HGFR-GFP=HGFR mutant where the whole intracellular portion was replaced by the GFP sequence.

Figure 9:
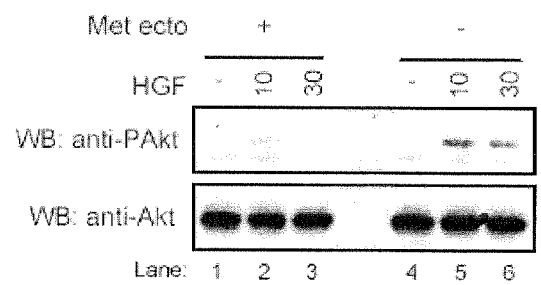

FIG. 9. The HGFR shed ectodomain behaves as a "decoy". Cells pre-treated with AntiMET-R were stimulated with HGF either in the absence or in the presence of HGFR ectodomain (Met ecto) in the culture medium. As shown, shed HGFR ectodomain impaired Akt activation and behaved as a "decoy".

Figure 10:
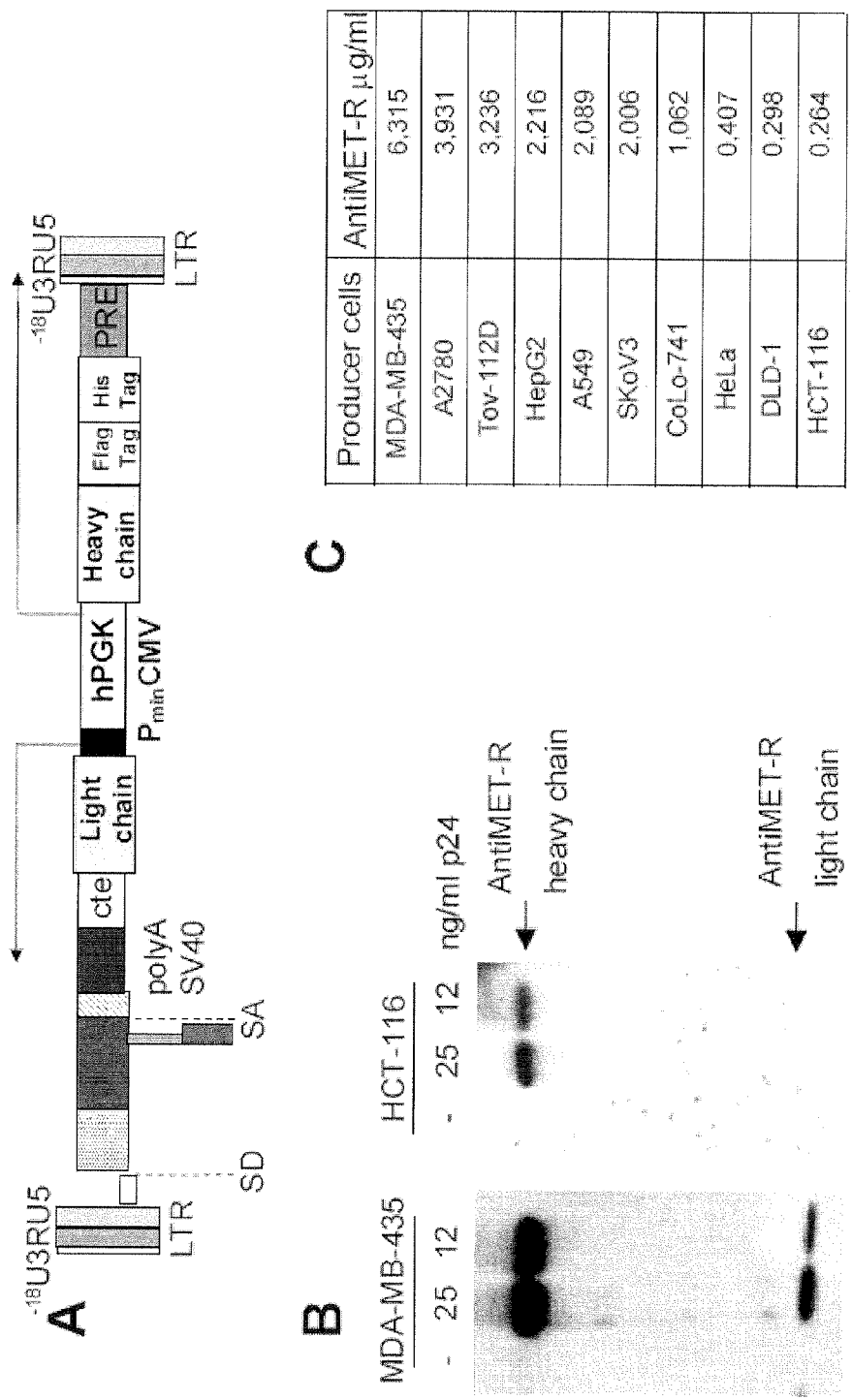

FIG. 10. Cells genetically modified by means of lentiviral vector mediated gene transfer express AntiMET-R. (A) Schematic drawing of the bi-directional lentiviral vector (integrated form) used to express AntiMET-R; LTR: HIV-1 Long Terminal Repeats; the U3 region is deleted at position −18 from R region. SD: Splice donor. SA: Splice Acceptor. PolyA SV40: polyadenylation site of the simian virus 40. Cte: constitutive transport element derived from the monkey Mason-Pfizer virus. $P_{min}CMV$: minimal promoter derived from CytoMegaloVirus. hPGK: human promoter of the Phophoglycerato Kinase gene. PRE: post-transcriptional regulatory element of the woodchuck hepatitis virus. FLAG Tag: sequence encoding 3 times repeated DYKDDDK epitope. His Tag: sequence coding 7 Histidine residues. (B) Western blot analysis of serum free culture supernatants (75 µl each sample) collected from two representative cell lines transduced with lentiviral vector carrying AntiMET-R cDNAs. Samples were subjected to SDS-PAGE under reducing condition and the corresponding filters were probed with antimouse Ig. (C) Table reporting the AntiMET-R quantification in culture supernatants derived from a panel of cell lines transduced with lentiviral vector carring AntiMET-R cDNAs.

Figure 11:
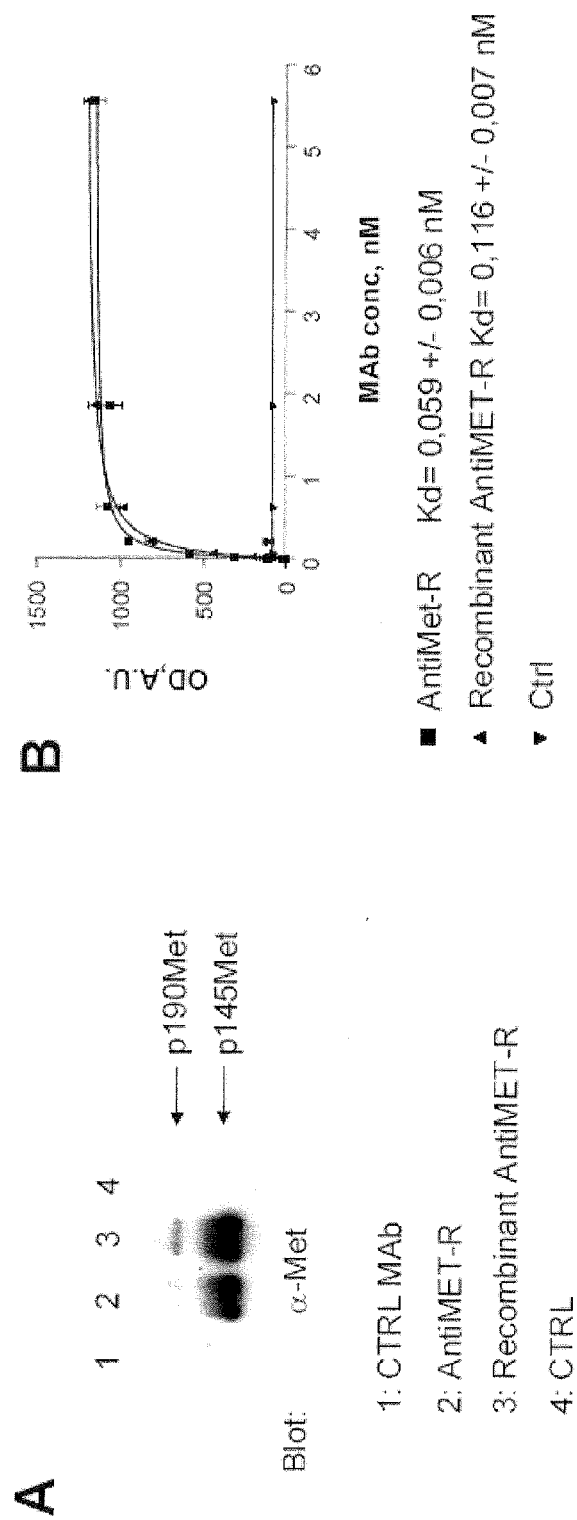

FIG. 11: The recombinant AntiMET-R binds with high affinity the extracellular domain of Met. (A) Western blot analysis of cell lysates containing the Met Receptor immunoprecipitated with the AntiMET-R derived from different sources (hybridoma or genetically modified carcinoma cell line). The immunoprecipitation was performed incubating Seph. Prot. G with cell culture supernatants from 1: Hybridoma producing unrelated MAb; 2 Hybridoma producing AntiMET-R MAb; 3: MDA-MB 435 cells infected with lentiviral vector carrying cDNAs for AntiMET-R MAb 4: MDA-MB 435 cells not infected. Samples were subjected to SDS-PAGE under reducing condition and the corresponding filters were probed with an anti-Met antibody directed against the c-Terminal tail of the receptor. (B) Binding assay of the AntiMET-R and the recombinant AntiMET-R to the extracellular domain of the Met Receptor. 96 wells plate coated with purified MET extracellular domain fused to the Fc domain derived from Human Ig (100 ng/well) was incubated with increasing concentrations of purified AntiMET-R or recombinant AntiMET-R (from 0 to 5.5 nM). Binding curve was revealed using anti-mouse Ig-HRP linked antibody. To control the specificity of binding we performed the same assay using wells coated with Fc-Ron (a chimera protein generated fusing the Fc domain of Human Ig to the extracellular domain of the Ron receptor, a protein belonging to the Met receptor family).

Figure 12:
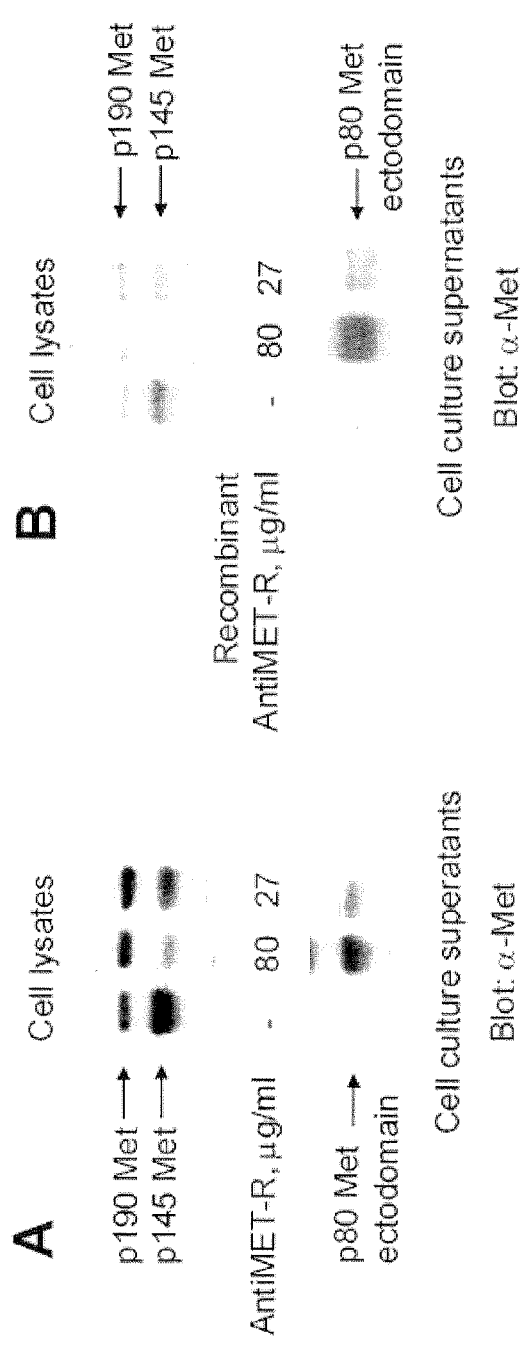

FIG. 12: The recombinant AntiMET-R induces the proteolytic cleavage of HGFR and shedding of the Extra-Cellular Domain (ECTODOMAIN). HCT-116 cells, a Colo-rectal carcinoma derived cell line, were incubated in serum free condition for 24 hrs with the indicated amount of purified AntiMET-R (A) or recombinant AntiMET-R (B). Total cell lysates (upper panels) and cell culture supernatants (lower panels) were subjected to SDS-PAGE followed by Western Blot. The decrease of mature Met (p145) form in the cells and the corresponding increase of Met ectodomain (p80) in the culture supernatants were monitored probing filters with DL-21 anti-Met mAb that recognizes a domain located in the extracellular portion of Met β chain.

Figure 13:
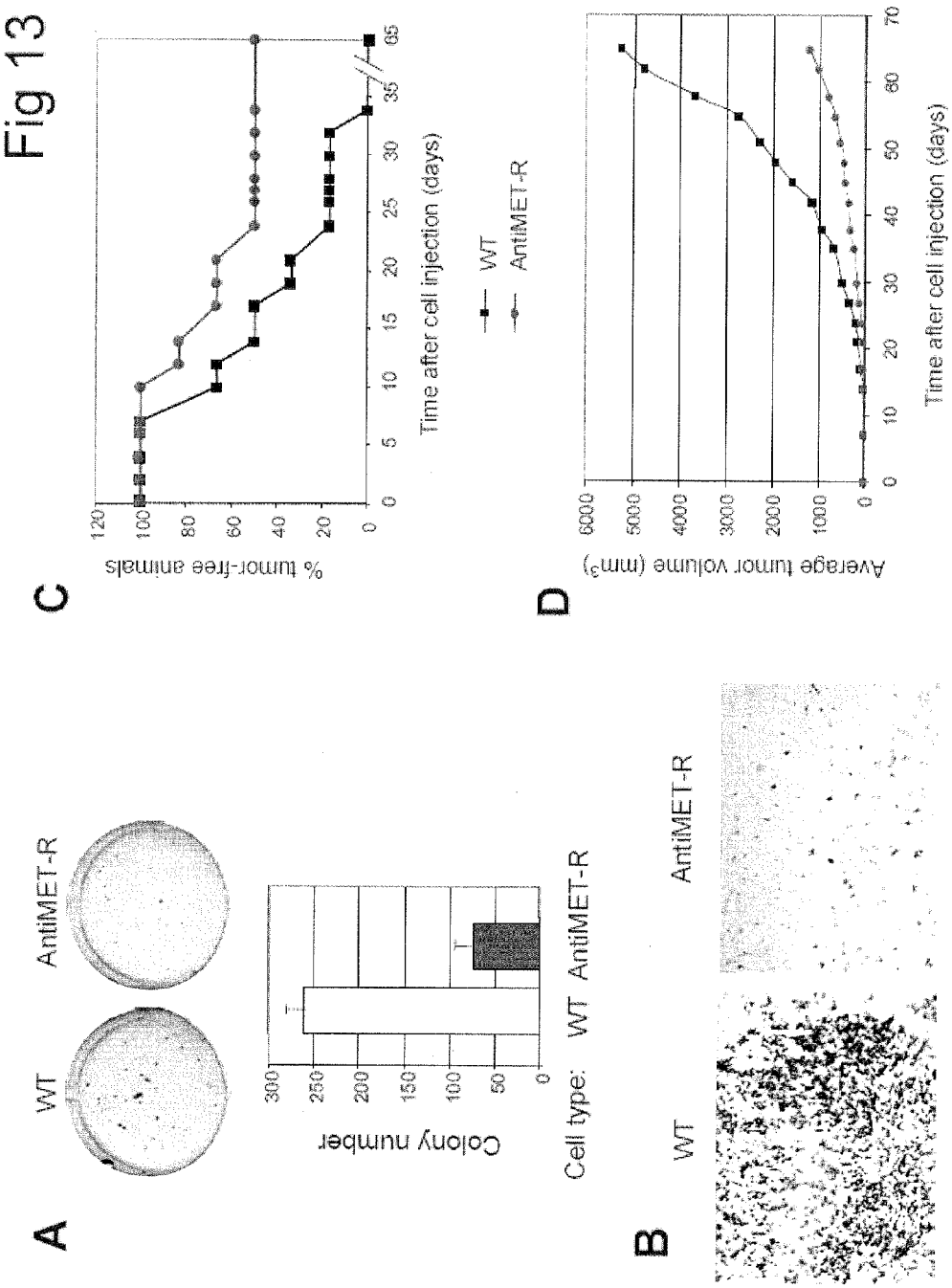

FIG. 13: Transduction with lentiviral vector encoding the AntiMET-R inhibits the transformed phenotype of cancer cells in vitro and in vivo. (A) Anchorage-independent growth assay. HCT-116 Cells transduced (AntiMET-R) or not (WT) with lentiviral vector encoding the AntiMET-R were seeded in 0.5% agar. Cells were then maintained in medium supplemented with 2% FCS+80 ng /ml HGF. Colonies were scored after 14 days; on the top a representative well is shown; on the bottom the graph represents the number of colonies (calculated from triplicates). (B) Invasion assay. HCT-116 cells transduced (AntiMET-R) or not (WT) with lentiviral vector encoding the AntiMET-R were plated on a matrigel-coated Transwell chamber. The lower chamber was filled with medium 2% FBS+80 ng/ml HGF. After 24 hrs cells attached to the lower part of the filters were scored. Pictures are representative fields of the filters. (C) In vivo tumor latency. HCT-116 cells transduced (AntiMET-R) or not (WT) with lentiviral vector encoding the AntiMET-R were injected sub-cute into the flank of athymic nude mice ($3 \times 10^6$ cells/mouse, n=6 for each group). Tumor mass was evaluated every 2 days with a caliper. Mice were considered positive for tumor presence when tumor mass exceeded 15 mm3. (D) In vivo tumor growth. HCT-116 cells transduced (AntiMET-R) or not (WT) with lentiviral vector encoding the AntiMET-R were injected sub-cute into the flank of athymic nude mice ($3 \times 10^6$ cells/mouse, n=6 for each group). Kinetic of tumor growth was evaluated measuring tumor mass with a caliper every 3 days. At the 65° day mice were all sacrificed.

Figure 14:
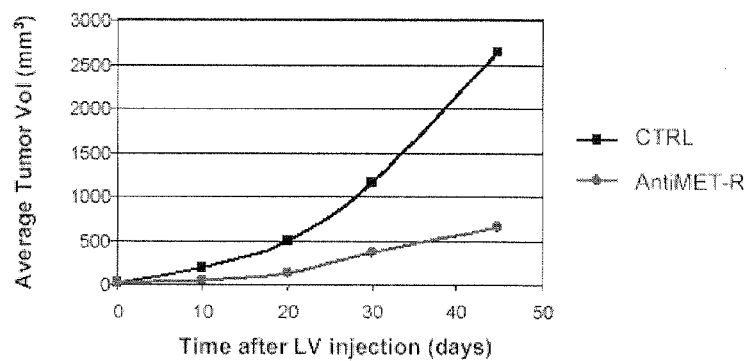

FIG. 14: Direct intra-tumor delivery of lentiviral vector encoding AntiMET-R inhibits tumor growth. HCT-116 cells ($4 \times 10^6$ cells/mouse) were injected sub-cute into the flank of athymic nude mice. When the tumor mass was around 10 mm3 tumors lentiviral vector particles (1 µg p24/mouse) were administrated intra-tumorally at day 0 and at day 3. One group (CTRL) received vector particles encoding GFP, while the other group received vector particles encoding Anti-MET-R (AntiMEt-R). Kinetic of tumor growth was evaluated measuring tumor mass with a caliper every 3 days.

Figure 15:
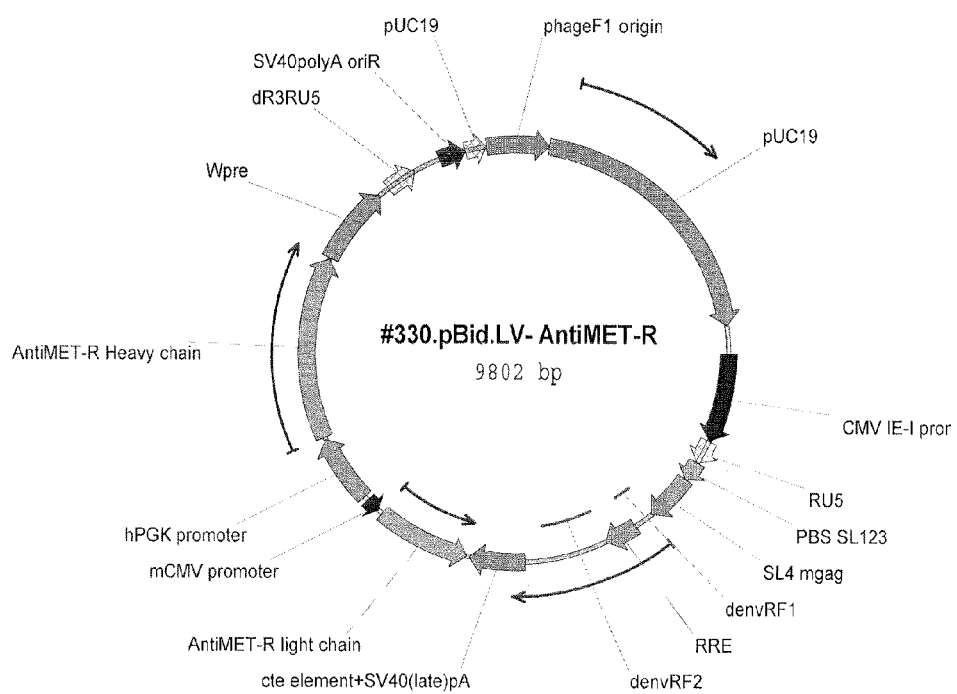

FIG. 15: Map of the plasmid encoding Anti-MET-R.

Figure 16:
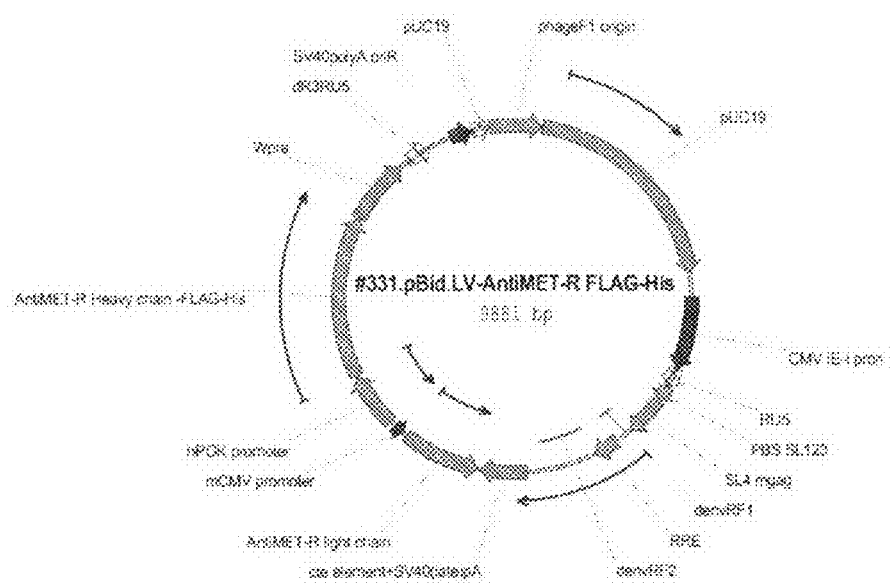

FIG. 16: Map of the plasmid encoding Anti-MET-R FLAG-His.

Figure 17:
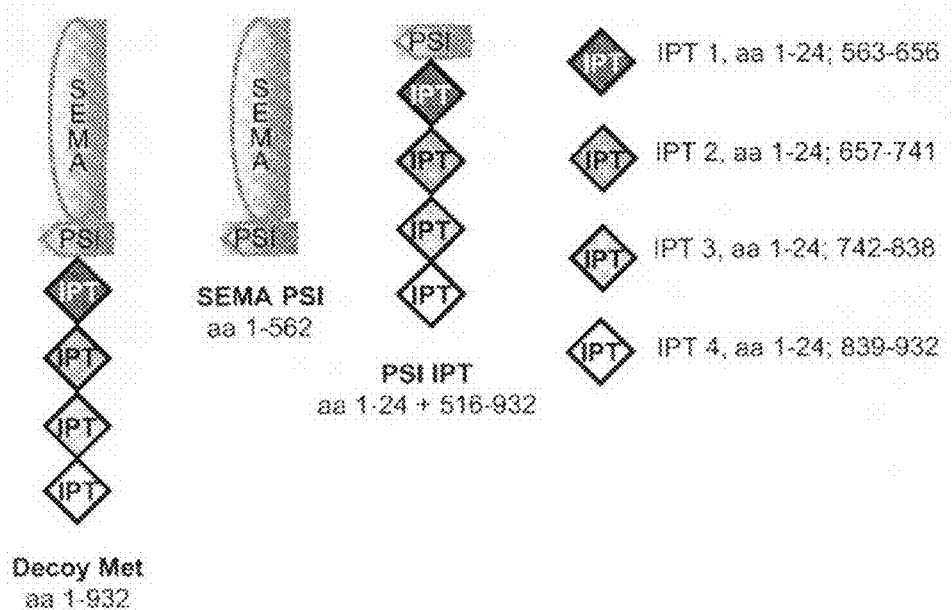

FIG. 17: Schematic drawing of the domains derived from the extracellular portion of the HGFR (Met ectodomain).

Figure 18:
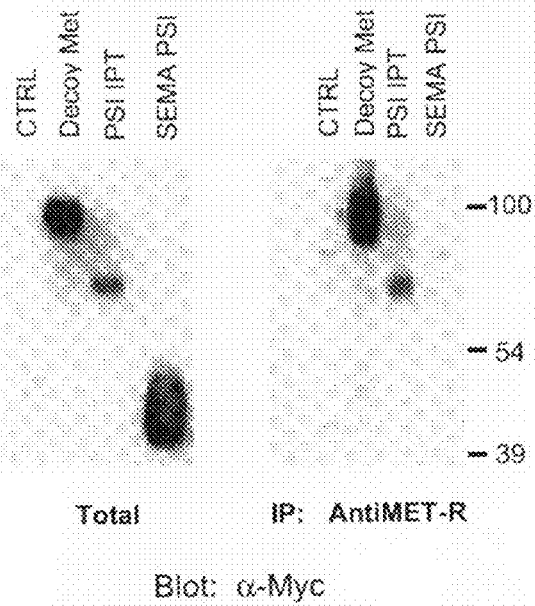

FIG. 18: AntiMET-R specifically recognizes an epitope located in the IPTs region. Conditioned media of MDA-MB-435 cells transduced with lentiviral vector particles encoding for myc-tagged Decoy Met, myc-tagged SEMA PSI and myc-tagged PSI IPT1-4 were immunoprecipitated with the anti-MET-R antibody and detected by Western blot using a biotinylated anti-myc antibody (right panel). Equal amounts of conditioned media were loaded as a control for protein expression (left panel). CTRL: conditioned medium of MDA-MB-435 cells transduced with an empty lentiviral vector. Decoy Met: conditioned medium of MDA-MB-435 cells transduced with a lentiviral vector expressing the entire HGFR extracellular domain. PSI-IPT: conditioned medium of MDA-MB-435 cells transduced with a lentiviral vector expressing PSI, IPT-1, IPT-2, IPT-3, IPT-4 domains of the HGFR. SEMA-PSI: conditioned medium of MDA-MB-435 cells transduced with a lentiviral vector expressing Sema and PSI domains of the HGFR. On the right molecular weight in KD are shown.

Figure 19:
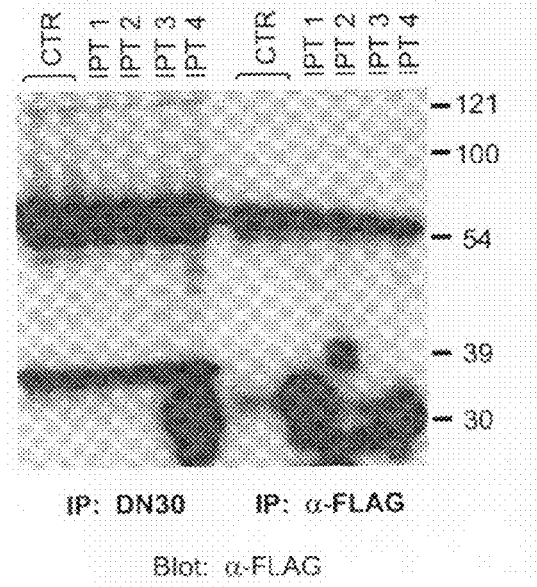

FIG. 19: AntiMET-R recognizes an epitope located in the IPT-4 region. Cell lysates of MDA-MB-435 cells transduced with lentiviral vector particles expressing IPT-1, IPT-2, IPT-3, IPT-4 single regions, all of them flag-tagged, were immunoprecipitated with the AntiMET-R antibody and detected by Western blot using an anti-flag antibody (left panel); as control for protein expression, similar amounts of cell lysates were immunoprecipitated with an anti-flag antibody and detected by Western blot using the same anti-flag antibody (right panel). CTRL: Cell Lysate from MDA-MB-435 cells transduced with an empty lentiviral vector. IPT1: Cell Lysate from MDA-MB-435 cells transduced with a lentiviral vector expressing the IPT-1 region of the HGFR. IPT2: Cell Lysate from MDA-MB-435 cells transduced with a lentiviral vector expressing the IPT-2 region of the HGFR. IPT3: Cell Lysate from MDA-MB-435 cells transduced with a lentiviral vector expressing the IPT-3 region of the HGFR. IPT4: Cell Lysate from MDA-MB-435 cells transduced with a lentiviral vector expressing the IPT-4 region of the HGFR. On the right molecular weight in KD are shown.

FIG. 20: AntiMet-R specifically stains the HGF receptor in intact cells. Panel A: Profile of GTL-16 analysed by flow cytometry with the antiMet-R antibody. Thin line: GTL-16 incubated with the isotype CTRL antibody; Bold line: GTL-16 incubated with AntiMet-R. MFI: Mean Fluorescence Intensity. Panel C: Immunofluorescence analysis of GTL-16 cells labeled with the AntiMet-R antibody revealed by a goat anti-mouse Ig conjugated with the fluorocrome Alexa Fluor 488. Panel B: GTL-16 cells labeled only with the anti-mouse Ig/Alexa Fluor 488. (Original magnification, x 63)

FIG. 21: Nucleic acid (a—SEQ ID NO:1) and aminoacid (b—SEQ ID NO:6) sequence of AntiMET-R heavy chain. The CDR regions (SEQ ID NOs:8, 9 and 10) are underlined both in the nucleotide and aminoacid sequence.

FIG. 22: Nucleic acid (a—SEQ ID NO:2) and aminoacid (b—SEQ ID NO:7) sequence of AntiMET-R light chain. The CDR regions (SEQ ID NOs:11, 12 and 13) are underlined both in the nucleotide and aminoacid sequence.

DETAILED DESCRIPTION OF THE INVENTION

The Hepatocyte Growth Factor Receptor, encoded by the MET proto-oncogene, is a tyrosine kinase receptor that, upon activation, elicits a complex spectrum of biological responses known as "invasive growth" (8). This implies induction and coordination of cell proliferation, migration, differentiation and survival. Under physiological conditions, this invasive growth program plays a pivotal role in organogenesis, during embryo development but, when unleashed in cancer, it contributes to tumor progression and metastasis (13).

The involvement of HGFR in human tumors is now firmly established, as germline missense mutations of the MET gene are responsible for some hereditary forms of cancer (9,10) and inappropriate HGFR activation has been shown in most types of solid tumors, often correlating with poor prognosis (14). The most frequent alteration in human cancers is receptor over-expression (15) that leads to constitutive dimerization and activation of the receptor, even in the absence of ligand (16). Increased HGFR expression can be due to (i) gene amplification, as in colorectal tumors, where MET confers to neoplastic cells a selective advantage for liver metastasis (11), (ii) enhanced transcription, induced by other oncogenes, such as Ras, Ret and Ets (17,18), (iii) hypoxia-activated transcription, in this case, the higher amount of receptor hyper-sensitises the cells to HGF and promotes tumor invasion (19).

Two strategies are currently used in clinical practice in order to interfere with tyrosine kinase receptors (RTKs): (i) treatment with small molecules inhibiting the tyrosine kinase activity; (ii) treatment with antibodies interfering with receptor activation.

The present invention is directed to the use in the tumor therapy of an anti-HGFR antibody, and in particular an anti-Met monoclonal antibody—called AntiMET-R—produced by the hybridoma cell line deposited by ICLC with accession number PD 05006, which was surprisingly found able to induce receptor down-regulation.

In one embodiment, the present invention involves the use of the monoclonal antibody AntiMET-R for the preparation of a medicament for the treatment of tumors and metastases in a patient suffering from a tumor.

In a further embodiment, the present invention concerns the use of the AntiMET-R antibody for the manufacture of diagnostic devices for the detection of neoplastic cells either in vivo or in vitro.

AntiMET-R is a monoclonal antibody (mAb) specific for the extra cellular domain of HGFR (20). This monoclonal antibody does not trigger all the biological effects elicited by hepatocyte growth factor (motility, proliferation, cell survival, invasion, tubulogenesis and angiogenesis) but it induces only motility. Moreover, it up-regulates the constitutive expression of urokinase-type plasminogen activator but it is not able to induce and sustain the expression of urokinase-type plasminogen activator receptor for prolonged periods of time. This mAb activates receptor phosphorylation, which, being strictly dependent on mAb bivalence, requires receptor dimerization.

The agonist ability of this antibody is not sufficient—per se—to justify its therapeutic activity. In fact, a different anti-MET-R monoclonal antibody (DO-24), that the inventors examined, is not able to induce an efficient receptor down-regulation and it does not promote shedding of the extracellular portion of the receptor.

AntiMET-R does not prevent interaction of HGFR with HGF, but efficiently promotes HGFR down-regulation as shown in Example 4 below and discussed with reference to FIG. 5. This interaction leads to inhibition of HGFR-mediated signal transduction and in particular of the Akt pathway, known to be involved in the anti-apoptotic response.

As it will be apparent from the results described below, the inventors demonstrated that in vitro treatment with Anti-MET-R resulted in impairment of cell ability to grow in an anchorage-independent manner (see Example 2 and FIG. 2), a property that requires the escape from apoptosis due to lack of anchorage. Moreover in vivo—as described in detail in Example 3—in animals treated with AntiMET-R, the present inventors have observed that tumors display an increased rate of apoptosis, without important changes in the proliferation rate. On the other hand, the inventors have not observed modification of cellular growth properties in response to the antibody, neither in vitro, nor in vivo, in agreement with lack of inhibitory effect of AntiMET-R on the activation of the MAPK pathway. This dissociation of the ability of HGFR to activate different pathways is not novel, it has already been shown for different HGFR mutants (21) and in response to HGFR partial agonists (22).

Antibody-induced HGFR down-regulation involves shedding of the extracellular portion of the receptor. Ectodomain shedding is a process in which the extracellular domain of membrane proteins is proteolytically released from the cell surface, thus allowing a cell to rapidly change its surface in response to environmental stimuli and to yield soluble regulators. The present inventors show evidence of this activity of AntiMET-R in Examples 6 and 7.

In the present application the inventors produce evidences—in particular in Example 3—that AntiMET-R antibody is active in vivo where it impairs tumor growth and formation of spontaneous metastases from cancer cells engrafted into nude mice. The experiments suggest that these effects are mediated by the action of the antibody both on cancer cells and on the microenvironment. In fact endothelial cells express HGFR (24) and we have demonstrated that the antiMet-R induces shedding of the HGFR also in this type of cells (data not shown). Neo-vascularisation of the primary tumor is an absolute requirement for both tumor growth and metastasis (23) and it has been firmly established that HGF is a potent angiogenic factor (24). Moreover upon HGFR activation, an increase in the release of the VEGF and other angiogenic factors occurs (48-49-40). Thus, the effect on tumor vascularisation could be also indirect as inhibiting Met function in tumor cells could abrogate the release of such factors from the tumor. The inventors of the present invention have observed a significant reduction of intratumor neovascularization, due to a decrease of the number of sprouting vessels of the microenvironment after treatment with Anti-MET-R.

It is worth nothing that the activity of AntiMET-R on host cells did not impact the functionality of different organs such as spleen, bone marrow, liver, heart, bone and kidney, which did not show evident pathological alterations (data not shown) after long-term exposure to the antibody. Thus, despite recognizing HGF-R in both normal and neoplastic cells, the AntiMET-R displays the ability to detect overexpression of HGF-R and to induce changes in cell viability.

In conclusion, the results shown herein suggest that AntiMET-R-induced down-regulation of HGFR is a candidate mechanism for immunotherapy and the use of AntiMET-R or fragments thereof in a pharmaceutical composition can provide a further way in the treatment of tumors and prevention of metastases in patients affected by tumor.

Additionally, AntiMET-R can be used as diagnostic tool to detect neoplastic cells either in vivo or in vitro, for example by labelling AntiMET-R with suitable labels.

AntiMET-R pursuant to the present invention can be produced by conventional methods in animals or, preferably, by genetic engineering techniques.

The use of the monoclonal antibody AntiMET-R according to the present invention is intended to include also the use of genetically engineered and humanized antibodies and antibodies labelled with suitable diagnostic markers. Genetically engineered and humanized antibodies and methods for their production are known in the art. See, for a review (25).

The use of AntiMET-R also include the use of fragments containing the epitope binding region thereof, such as peptides containing the epitope binding region or Complementarity Determining Regions (CDRs), Fv, scFv, Fab, Fab', F(ab')$_2$ fragments. Conventional fragments are typically produced by proteolitic cleavage, but can also be produced by chemical synthesis, such as liquid or solid phase synthesis, as well as by recombinant DNA techniques.

AntiMET-R and its fragments are preferably used in pharmaceutical compositions in the form of soluble protein, whose delivery may be achieved using conventional methods of drug delivery. Administration of pharmaceutical compositions comprising the antibody AntiMET-R and/or fragments thereof may be accomplished by any method known to the skilled person. For instance, the composition can be administered in an aqueous solution which is injected or infused into the patient. The determination of the proper dosage depends upon a number of case specific variables, including the age and weight of the patient and involve routine experimentation within the expertise of the skilled person.

Another embodiment of the present invention involves the production of pharmaceutical compositions containing the monoclonal antibody AntiMET-R labelled with a suitable diagnostic marker for the detection in vivo or in vitro of neoplastic cells in a patient suffering from a tumor.

The present invention involves the production of a DNA vector comprising a synthetic promoter obtained joining a minimal core promoter (minCMV promoter) upstream in an opposite orientation to the efficient promoter of the human Phosphoglycerato Kinase gene and DNA encoding at least a portion of the monoclonal antibody AntiMET-R. The DNA sequences comprised in the vector encode the light and/or heavy chain of AntiMET-R; conservative substitutions in the DNA sequences are also encompassed by the present invention as well as sequences modified by the addition of tag sequences both at the 5' or 3' terminal. The nucleotide sequences encoding the heavy and light chain of AntiMET-R are represented in SEQ ID No.: 1 and SEQ ID No.:2, respectively.

Moreover the inventors modified the heavy chain adding a tag sequence to the 3' of the AntiMET-R heavy chain (SEQ ID No.: 3). This sequence allows purification of the MAb using a Nichel column and is recognized specifically by anti-FLAG antibodies (SIGMA).

Although the production of the DNA vectors of the present invention may be accomplished by a variety of methods known in the art, production is exemplified in Example 10.

In another embodiment, the present invention involves the use of a DNA vector comprising DNA encoding the epitope biding region of the monoclonal antibody AntiMET-R for the preparation of a medicament for the treatment of tumor and metastases in a subject. The delivery of the DNA vectors of the present invention may be achieved using known methods of gene therapy. For example make reference to (10).

A further embodiment of the present invention involves a product comprising the antibody AntiMET-R and/or fragments thereof and kinase inhibitors as a combined preparation for simultaneous, separate or sequential use in tumor therapy. Examples of kinase inhibitors which can be advantageously used in the present invention are K252A staurosporin analogue (Calbiochem-Novabiochem Intl.; 36); PHA-665752 (3Z)-5-[(2,6-dichlorobenzyl)sulfonyl]-3-[(3,5-dimethyl-4-{[(2R)-2-(pyrrolidin-1-ylmethyl)pyrrolidin-1-yl]carbonyl}-1H-pyrrol-2-yl)methylene]-1,3-dihydro-2H-indol-2-one (34); SU11274 [(3Z)-N-(3-chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide] (37,38,35); SU11271 [(3Z)-5-(2,3-dihydro-1H-indol-1-ylsulfonyl)-3-({3,5-dimethyl-4-[(4-methylpiperazin-1-yl)carbonyl]-1H-pyrrol-2-yl})methylene)-1,3-dihydro-2H-indol-2-one] (38); SU11606 [(3Z)-N-(3-chlorophenyl)-3-{[3,5-dimethyl-4-(3-morpholin-4-ylpropyl)-1H-pyrrol-2-yl]methylene}-N-methyl-2-oxoindoline-5-sulfonamide] (38).

The inventors have, in fact, observed that the inhibitory mechanism activated by AntiMET-R does not require HGFR tyrosine kinase activity. This feature represents a relevant advantage in a therapeutic approach. In clinical practice, in fact, it is frequent to combine different drugs in order to improve the effect on the target molecule. In the case of HGFR, it is thus possible to combine kinase inhibitors with the antibody, allowing the contemporary action both on HGFR activation and levels. This is likely to enhance the therapeutic efficacy of target therapy in Met-overexpressing tumors, with the aim of interfering both with tumor growth and with the acquisition of an invasive-metastatic phenotype.

The antibody AntiMET-R and its fragments part of the product according to the present invention are produced as specified above. The kinase inhibitors to be used in the combined preparation according to the present invention can be produced by conventional chemical synthesis or genetic engineering techniques.

In a further embodiment, the present invention encompasses a method for screening compounds able to bind to at least one portion of the extra cellular domain of Hepatocyte Growth Factor Receptor, wherein these compounds have an antagonist activity versus the Hepatocyte Growth Factor Receptor and are pharmacologically active in the prevention and/or treatment of tumor and/or metastases. In particular, these compounds are able to induce Hepatocyte Growth Factor Receptor down-regulation or shedding of at least a portion of the extra cellular domain of Hepatocyte Growth Factor Receptor.

The present invention will now be described in relation to some preferred embodiments by way of non-limiting examples.

Antibodies, Inhibitors and Other Reagents.

Monoclonal anti-HGFR AntiMET-R was originally described by Prat (20). Other antibodies used for Immunoprecipitation and western blot analysis are: anti-HGFR antibodies DO24 and DL21 (recognizing HGFR extracellular domain described in 20); anti-phosphotyrosine PY20 (Transduction Laboratories), anti-ubiquitin (Babco), anti-Hsp70 (Stressgen), anti-phospho Akt (Ser473, Cell Signaling Technology), anti-Akt (Santa Cruz Biotechnologies) anti-HGFR intracellular domain (C12, Santa Cruz Biotechnologies). Immunohistochemical stainings were performed with: anti human phospho-HGFR (Cell Signaling) and anti-mouse CD31 antibody (Pharmingen). For in vitro and in vivo experiments anti-vesicular stomatitis virus antibody (VSV-G, Sigma) was used as a control. Lactacystin and concanamycin were purchased from Calbiochem.

AntiMET-R Nucleotide and Aminoacid Sequences.

The translation of the AntiMET-R heavy chain nucleotide sequence corresponding to the SEQ ID No.: 1 and FIG. 21a is reported in FIG. 21b and SEQ ID No:6.

The nucleotidic and amminoacid sequences corresponding to the CDR regions are underlined in FIGS. 21a and 21b; their amminoacid sequences are: CDR-H1: GYTFTSYW (SEQ ID NO.:8); CDR-H2: INPSSGRT (SEQ ID NO.:9); CDR-H3: ASRGY(SEQ ID NO.:10).

The translation of the AntiMET-R light chain nucleotide sequence corresponding to the SEQ ID No.: 2 and FIG. 22a is reported in FIG. 22b and in SEQ ID NO.:7.

The nucleotidic and amminoacid sequences corresponding to the CDR regions are underlined in FIGS. 22a and 22b; their amminoacid sequences are: CDR-L1: QSVDYDGGSY (SEQ ID NO.:11); CDR-L2: AAS (SEQ ID NO.:12); CDR-L3: QQSYEDPLT (SEQ ID NO.:13).

Transient Transfection of 293T Cells for Lentiviral Vectors Production.

Approximately 24 hours before transfection $6.0 \times 10^6$ 293T cells were seeded in a 15 cm dish. 2 hours before transfection culture medium was changed adding 22 ml of IMDM, supplemented with heat inactivated FBS (10%), Penicillin (25 U/ml), Streptomycin (25 U/ml) and Glutamine (1%). The plasmid DNA mix for transfection was prepared by adding: ENV plasmid (VSV-G), 9 µg; PACKAGING plasmid pMDLg/pRRE 16.2 µg; REV plasmid, 6.25 µg; TRANSFER VECTOR plasmid #330 or #331, 37.5 µg. The plasmid solution was made up to a final volume of 1125 µl with 0.1×TE/dH$_2$O (2:1). 125 µl of 2.5M CaCl$_2$ were added and left at RT for 5'. Then, vortexing at full speed, 1250 µl of 2×HBS solution were added and than immediately added drop wise to the cell culture. CaPi-precipitated plasmid DNA incubated for 14-16 hours, then medium, was replaced with fresh one added of 1 mM sodium butyrate (18 ml per dish). Cell culture supernatant, containing vector particles, was collected at 30-36 hours after changing the medium. After collection, the supernatants were spin at 2500 RPM for 10', filtered through 0.2 µm and stored at −80° C.

Infection of Target Cells by Cell Supernatant Containing Lentiviral Vector.

$10^5$ cells were seeded with fresh culture medium supplemented with 10% FBS, glutamine. For infection cell lines were incubated, in the presence of polybrene 8 µg/ml, with supernatant containing lentiviral vector particles prepared as described above at final concentration of vector particles between 10 and 150 ng/ml of HIV-1 Gag p24 equivalent (measured by ELISA assay). After 18 hrs the medium was changed and the cells were let grow. When the culture was 80% confluent, cells were incubated with medium without serum and after 72 hrs supernatant containing AntiMET-R was collected.

HGFR Down-Regulation Assay.

Cells were maintained in Dulbecco's modified Eagle's medium (DMEM) supplemented with 10% fetal bovine serum. Treatments with the antibodies and HGF were performed in serum free medium with 80 µg/ml and 80 ng/ml, respectively. Where indicated, cells were pre-incubated for 2 hrs with either 10 µM lactacystin or 100 nM concanamycin, prior to stimulation. For the analysis of HGFR degradation, cells were lysed in LB buffer (2% SDS, 0.5 M Tris-Hcl pH=6.8) and protein concentration in cell lysates was evaluated with the BCA Protein Assay Kit (Pierce). Then, equal amounts of total proteins were analysed by SDS-PAGE and Western Blotting. For immunoprecipitation experiments, cells were lysed in EB buffer (20 mM Tris-HCl, pH 7.4, 5 mM EDTA, 150 mM NaCl, 10% glycerol, 1% Triton X-100) in the presence of protease inhibitors and 1 mM Na-orthovanadate. After immunoprecipitation with the appropriate antibodies, high stringency washes were performed. Then immunoprecipitated proteins were processed for Western Blotting according to standard methods. Final detection was performed using the ECL detection system (Amersham).

Metabolic Labelling and Analysis of HGFR Shedding.

Cells were serum starved for 16 hours, pulse-labeled with [$^{35}$S] methionine and [$^{35}$S] cysteine (100 µCi/ml, Amersham Corp.) for 30 min. in methionine- and cysteine-free DMEM medium and then treated with either AntiMET-R or VSV-G or HGF for 4 hours. Conditioned media were collected and subjected to immunoprecipitation with anti-HGFR extracellular antibody. Immunoprecipitated proteins were separated by SDS-PAGE and autoradiography was performed as previously described in (26).

In Vitro Biological Assays.

For evaluation of anchorage-independent growth, GTL16 were pre-treated with either AntiMET-R or VSV-G in spent medium for 48 hours. Then 1,500 cells were seeded in DMEM 2% FBS plus 0.5% soft agar (SeaPlaque agarose, BMA) in each well and maintained in the presence of the indicated amounts of antibodies and HGF for 10 days. Grown colonies were finally visualised by tetrazolium staining (47). The invasion assay was performed in Transwell chambers (Corning). The polycarbonate filters (8 µm pore size) were coated with 15 µg/cm$^2$ of Matrigel basement membrane (Collaborative Research). Antibody treatment was performed pre-incubating the cells for 24 hours before seeding with 20 nM AntiMET-R or VSV-G. Then $5 \times 10^4$ cells were seeded on the upper side of the filters and incubated in DMEM+2% FBS with 100 ng/ml HGF added in the bottom wells of the chambers. After 48 hours, cells on the upper side of the filters were mechanically removed. Cells migrated to the lower side were fixed, stained and counted. The migration index was obtained by dividing the number of cells migrated on HGF stimulation by the ones migrated without.

In Vitro Labelling of the HGFR with AntiMet-R.

For Flow cytometry analysis, $10^5$ GTL-16 cells were detached with PBS-EDTA 0.025%, washed with PBS and incubated with 50 µg/ml of antiMet-R antibody or the same amount of isotype control mouse Ig for 15' RT. After 2 washes with PBS, the cells were incubated with 15 µg/ml of FITC conjugated Goat anti-mouse Ig (Jackson Immunoresearch laboratories) for 15' RT. Cells were than washed, re-suspended in PBS-5% BSA and analysed by flow cytometry (Becton Dickinson, Mountain View, Calif.). GTL-16 cells were fixed in methanol:aceton (3:1) for 5' on ice then blocked with 2% goat serum in PBS for 30' at RT. Purified antiMet-R was added at a concentration of 2.5 µg/ml in PBS 2% goat serum and incubated 1 hr RT, than after 3 washes with PBS, bound anti-HGFR antibody was revealed with 4 µg/ml of anti-mouse Ig conjugated with the Alexa Fluor 488 (Molecular Probes). Analysis of the samples was performed with a fluorescence microscope (DM-IRB, Leica Microsystems).

In Vivo Experiments.

The in vivo experiments were performed by inoculating subcutaneously either $1 \times 10^6$ GTL16 or $2.5 \times 10^6$ MDA-MB-435β4 into the posterior flank of six-weeks-old immunodeficient nu/nu female mice on Swiss CD1 background (Charles River Laboratories). Upon appearance of the tumor, mice bearing masses of comparable size were selected and inoculated either I.P. or I.S. (I.S. only, in the case of GTL16 injected mice) twice a week with the indicated amounts AntiMET-R and anti-VSV-G. After 8 weeks of treatment, mice were sacrificed and tumor weight was evaluated. In mice injected with MDA-MB 435β4 the lungs were analysed for the presence of spontaneous metastasis. Immunohistochemical staining of primary tumors for evaluation of phosphorylated HGFR was performed on 5 µm paraffin embedded tumor sections using an anti-phospho-HGFR antibody (Cell Signaling, 1:100). The number of metastases was established by means of microscopical observation of the lungs after hematoxylin/eosin staining performed according to the Masson-Trichrome protocol (Sigma) for routine pathological investigation. Evaluation of tumor vascularization was performed by immunohistochemistry on samples embedded in Tissue-Tek OCT compound (Sakura Finetek) and immediately frozen at −80° C. For the immunohistochemical stainings a rat monoclonal anti-mouse CD31 antibody (Pharmingen) was used.

Evaluation of Apoptosis.

Morphological assessment of apoptosis was evaluated according to Kerr's criteria. Because of the large number of single necrotic cells and ischemia-induced apoptosis close to necrotic foci, only tissue at least 1 HPF (High Power Field=0.63 mm) far from the areas of necrosis was considered reliable for the apoptotic count. Cases with massive tumoral necrosis were not evaluated. All cases were lumped in one of the two categories: more or less than 10 apoptotic figures/10 HPF.

Inhibition of Proteases

Prior to antibody stimulation cells were treated for 2 hours with the following inhibitors: 4 mM amiloride (Sigma) to inhibit Urokinase; 5 mM 1,10-phenantroline (Sigma) to inhibit ADAM and Zn-dependent proteases; 20 µg/ml aprotinin and 100 µg/ml leupeptin to inhibit serine and cystein proteases, 10 µg/ml pepstatinA to inhibit acid proteases (Calbiochem). PKC was inhibited by treating cells with 1 µM TPA for 24 hrs.

Screening Methods

The invention provides assays for screening test compounds which modulate the expression/function/biological activity of the HGFR or induce shedding of the extra cellular domain of HGFR in presence or absence of HGF or other receptor agonists.

A test compound binds to HGFR preferably interacting with the receptor extracellular portion. More preferably, a test compound decreases a biological activity mediated via HGFR by at least about 10, preferably about 50, more preferably about 75, 90, or 100% relative to the absence of the test compound.

A further test compound preferably regulates expression of HGFR. More preferably, a test compound down-regulates HGFR transcript or protein by at least about 10, preferably about 50, more preferably about 75, 90, or 100% relative to the absence of the test compound.

Test Compounds

Test compounds can be pharmacological agents, peptides or proteins already known in the art or can be compounds previously unknown to have any pharmacological activity. Test compounds can be naturally occurring or designed in the laboratory. They can be isolated from microorganisms, animals, or plants, can be produced by recombinant techniques or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds.

Binding Assays

For binding assays, the test compound is preferably a molecule which binds to HGFR extracellular portion, where said molecule mimics the AntiMet-R activity such that the normal biological activity of HGFR is prevented. Examples of such molecules include, but are not limited to, small molecules, peptides or peptide-like molecules.

In binding assays, either the test compound or HGFR extracellular portion can comprise a detectable label, such as a radioisotopic, fluorescent, chemiluminescent, or enzymatic label (e.g. radiolabelled iodine, radiolabeled phosphorus, fluorophores or fluorescent proteins, luciferase, horseradish peroxidase or alkaline phosphatase). Detection of a test compound which is bound to the HGFR extracellular domain can then be accomplished, for example, by direct counting of radioemission, by scintillation counting, or by determining conversion of an appropriate substrate to a detectable product, where HGFR or a portion of its extracellular domain is bound to a support or expressed by a cell or can be retrieved according to well know methods to an expert in the field.

Functional Assays

Test compounds can be tested for the ability to decrease a biological effect of HGFR. Such biological effects can be determined using the functional assays described in the present application. They are referred as the anchorage independent growth assay and the invasion assay (both described in detail in the examples 2 and 11) and the evaluation of the transformed phenotype in vivo (described in detail in the examples 3, 11, 12). Thus, functional assays can be carried out in vitro, using any cell line expressing HFGR or in vivo using any animal model in which is possible to study the development of an experimental or naturally occurring tumor expressing the HGFR. A test compound which decreases a biological activity of HFGR by at least about 10, preferably about 50, more preferably about 75, 90, or 100% is identified as a potential pharmacological agent for decreasing HGFR biological activity.

EXAMPLES

Example 1

The Anti-Met Antibody AntiMET-R Impairs HGFR Signal Transduction

AntiMET-R is a monoclonal antibody directed against the extracellular domain of HGF receptor where it recognizes an epitope distinct from that bound by the ligand. This mAb behaves as a partial agonist, since it does not trigger all the biological effects elicited by hepatocyte growth factor (motility, proliferation, cell survival, invasion, tubulogenesis and angiogenesis) but it induces only motility. Moreover, it up-regulates the constitutive expression of urokinase-type plasminogen activator but it is not able to induce and sustain the expression of urokinase-type plasminogen activator receptor for prolonged periods of time. This mAb activates receptor phosphorylation, which, being strictly dependent on mAb bivalence, requires receptor dimerization.

To address the question of whether the AntiMET-R antibody might represent a tool to interfere with constitutive HGF receptor activation in over-expressing tumours, the inventors first analysed its biochemical and biological activity in tumor cells chronically exposed to the antibody. As a model, the inventors used GTL16 cells, derived from a human gastric carcinoma, where HGFR is over-expressed and therefore oligomerized and constitutively activated (27). FIG. 1A shows, a significant reduction in HGFR expression and tyrosine phosphorylation.

The effect of the antibody on HGFR signal transduction was then evaluated. Since HGFR is known to promote a strong anti-apoptotic program by stimulating Akt activation, the inventors evaluated the level of Akt phosphorylation upon AntiMET-R treatment. As shown in FIG. 1B, Akt phosphorylation was inhibited both in basal condition and in HGF-stimulated cells.

Another important pathway activated by HGFR is the MAPK pathway, known to be involved in stimulation of cell growth. The inventors checked the level of activation of MAPKs in cells treated with the antibody, but did not observe significant inhibition of this pathway (data not shown).

Example 2

AntiMET-R Inhibits the Transformed Phenotype of Cancer Cells In Vitro

The effect of the antibody on cell growth and on the transformed phenotype was assessed by measuring the ability of cells to grow in anchorage-dependent and -independent manner and to invade extra-cellular matrices. As shown in FIG. 2A, no difference in the ability of cells to grow in conditions of anchorage dependency was observed upon antibody treatment.

Anchorage-independent growth is strictly dependent on the ability of cells to overcome apoptosis due to lack of anchorage, the so-called "anoikis"; this property is usually analysed by evaluating the capability of cells to grow in soft agar (28). Since many reports have shown that HGFR activation is able to confer to cells this property, the inventors seeded GTL16 cells in 0.5% agar and maintained the culture in the presence or absence of different amounts of Anti-MET-R or of an irrelevant isotype-matched antibody (VSV-G), as a control. As shown in FIG. 2B, VSV-G treated as well as untreated cells were able to form numerous colonies. Conversely, AntiMET-R drastically inhibited anchorage-independent growth of cancer cells in a dose-dependent manner. It is interesting to note that GTL16 cells were able to form colonies in soft agar assay even in basal condition, due to constitutive HGFR activation, and that the antibody reduced the transformed phenotype of these cells both in the presence and in the absence of HGF.

To evaluate the ability of the antibody to interfere with cell invasiveness, the inventors studied MDA-MB-435 β4, a mammary carcinoma cell line which, in response to HGF, is able to invade reconstituted basement membranes (29). As shown in FIG. 2C, in vitro treatment of these cells with AntiMET-R resulted in a dose-dependent reduction of invasive properties in response to HGF.

Example 3

AntiMET-R Inhibits the Transformed Phenotype In Vivo

Figure 3:
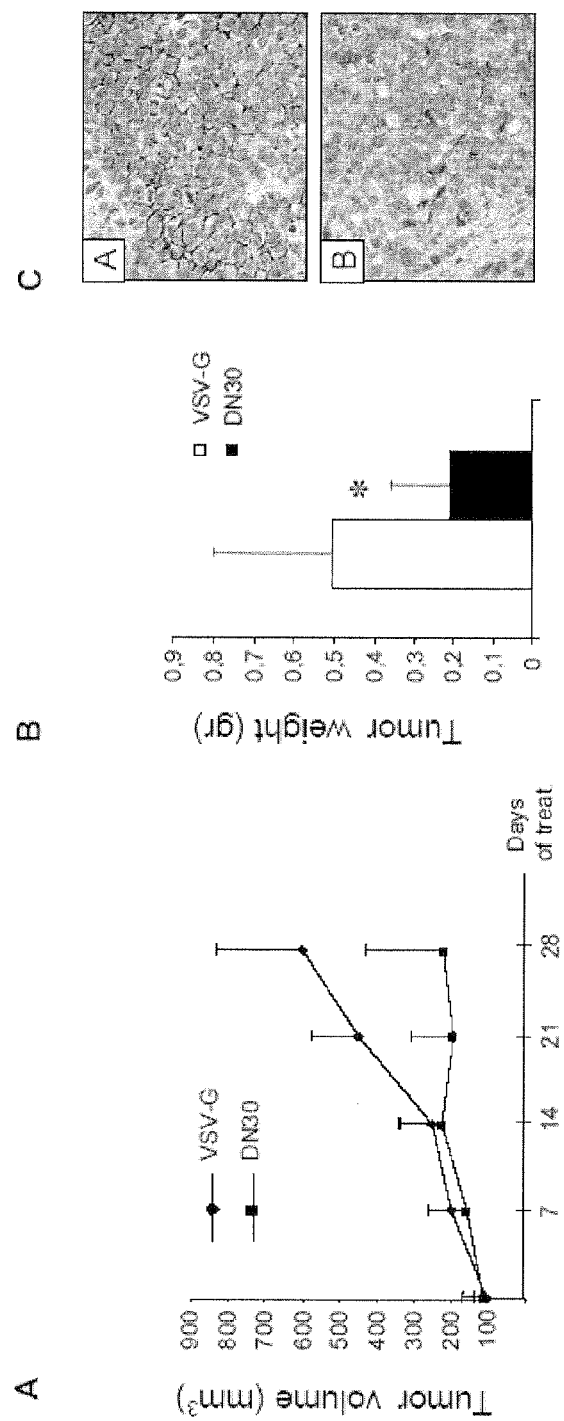
FIG. 3. AntiMET-R inhibits the transformed phenotype of cancer cells in vivo (A, B) Tumorigenesis assay. Nude mice were injected subcutaneously with $1.5 \times 10^6$ GTL16 cells. After tumor appearance, mice displaying tumors of the same size were selected and then injected in situ twice a week with 2 μg/gr of either VSV-G or AntiMET-R. Tumor volume was measured at different time points (A). As shown, AntiMET-R impaired tumor growth in nude mice engrafted with human tumor cells. Mice were sacrificed after 8 weeks of treatment and tumor weight was evaluated (B). In mice treated with AntiMET-R, tumors were significantly smaller than in control mice ($p<0.05$). (C) Evaluation of HGFR activation. Tumor sections from mice treated with VSV-G (panel A), or AntiMET-R (panel B) were stained with anti-human phospho-HGFR.

To assess the activity of AntiMET-R on tumor growth in vivo, the inventors inoculated subcutaneously GTL16 cells into the posterior flank of immunodeficient nu/nu female mice. The animals were treated twice a week with either AntiMET-R or VSV-G, administered in situ (2 µg/gr). The therapy started 1 week after transplantation, upon appearance of tumors in the site of injection: only animals bearing tumors of comparable size were treated for 4 weeks. Tumor volume was monitored during all treatment and a decreased growth was observed in AntiMET-R treated mice (FIG. 3A), After treatment, mice were autopsied and tumors were excised and weighed. As shown in FIG. 3B, in mice treated with Anti-MET-R, tumors were significantly smaller than in controls ($p<0.05$). In these tumors the level of HGFR activation, shown by staining with specific antibodies against the phosphorylated form of the receptor, was decreased (FIG. 3C) while the percentage of apoptotic cells was significantly increased (FIG. 3D). Moreover the present inventors evaluated in the tumor sections after staining with hematoxylin/eosin apoptotic and mitotic figures. While apoptosis was significantly increased in tumor tissues obtained from mice treated with the AntiMET-R, the number of mitoses was almost unchanged (data not shown).

The inventors performed the same kind of experiments also on MDA-MB-435 β4 cells, a model system for in vivo spontaneous metastasis (29). Animals were treated twice a week with different doses of AntiMET-R or the control antibody, administered either systemically (1 µg/gr or 10 µg/gr intraperitoneally) or into the tumour (2 µg/gr in situ). The therapy started at the day of transplantation and was carried out for eight weeks (the time for the metastatic potential to be expressed). After treatment, mice were autopsied and analysis of primary tumours and lungs (the privileged site of metastases for these cells) were performed. Different organs (spleen, bone marrow, liver, heart, bone and kidney) were also examined to rule out potential toxic effects. Macroscopic analysis showed that AntiMET-R treatment resulted in growth inhibition of the primary tumour mass (FIGS. 4A-E and K). Immunohistochemical staining with antibodies recognising the tyrosine-phosphorylated form of HGFR showed, also in this case, a marked reduction of receptor activation (FIG. 4F-J). Moreover, microscopic analysis of the lung sections revealed that both intra tumor injection and systemic administration of AntiMET-R prevented the appearance of distant metastases in the lung and in the inspected organs (FIG. 4L).

Since many works have shown that HGF is a potent angiogenic factor and that HGFR signalling contributes to tumor angiogenesis, the inventors analysed tumor vascularization upon AntiMET-R treatment. In these tumors the inventors found a significant reduction of the number of vessels (which were fewer and larger in size) and of their branches (FIG. 4 M,N). The inventors thus conclude that the observed anti-tumor and anti-metastatic effect of the treatment was due to the combined action of the antibody on tumor and on sprouting vessels of the microenvironment.

Example 4

AntiMET-R Induces HGFR Down-Regulation

To study the mechanism through which AntiMET-R is able to interfere with HGFR activation, the inventors treated with either AntiMET-R or VSV-G, HGFR overespressing cells; this instance resembles what is frequently observed in many naturally occurring tumors. As shown in FIG. 5A, the inventors observed that the total amount of HGFR decreased, in a time-dependent manner, upon AntiMET-R but not VSV-G treatment. This suggests that the anti-Met antibody specifically induced receptor down-regulation. It is interesting to underline that in these cells, over-expressing HGFR, HGF, the ligand, was unable to induce receptor down-regulation (FIG. 6, lower panel).

The inventors then verified whether the AntiMET-R antibody could trigger receptor down-regulation also in cells expressing normal levels of HGFR. As shown in FIG. 5B, left panel, also in these cells, AntiMET-R efficiently down-regulated HGFR.

Antibody-induced reduction of HGFR exposed at the cell membrane was also evaluated by FACS analysis. The cytofluorimetric analysis showed that antibody treatment reduced the amount of HGFR expressed at the cell surface with efficiency higher than HGF itself (FIG. 5B, right panel). A similar reduction, in the same assay, was observed also in GTL16 cells (not shown).

Example 5

Molecular Mechanism of AntiMET-R-Induced HGFR Down-Regulation

Ligand-dependent and antibody-induced down-regulation may follow different pathways. Ligand-dependent down-regulation of RTKs is a multistep process including internalisation, ubiquitinylation, endosomal sorting and finally lysosomal or proteasomal degradation (30).

To assess which degradation pathway is involved in antibody-induced HGFR down-regulation, the inventors blocked the activity of either the lysosome or the proteasome with the specific inhibitors concanamycin and lactacystin, respectively, prior to antibody stimulation. Surprisingly, while inhibition of the proteasomal pathway severely impaired ligand-induced HGFR degradation, it did not affect receptor down-regulation due to AntiMET-R treatment (FIG. 6A, upper panel), thus indicating that the antibody and the ligand promote HGFR down-regulation through different molecular mechanisms. Moreover, when the activity of the proteasome was impaired, a fragment of 60 Kd, barely detectable in basal condition, was heavily accumulated in cells upon antibody treatment (FIG. 6A, lower panel). This fragment was detectable on Western blots only with an anti-intracellular HGFR antibody and consisted in the cytoplasmic domain of the receptor. Moreover, as expected for molecules committed to proteasomal degradation, the 60 Kd fragment was tagged with ubiquitin moieties (FIG. 6B).

As the extracellular domain (Ectodomain) of the receptor was not detectable in cell lysates upon AntiMET-R treatment, the inventors verified whether it was released outside the cells upon cleavage, a phenomenon known as "shedding" (31). To test this hypothesis the inventors looked for the presence of the HGFR ectodomain in cell culture medium. Cells were metabolically labelled with radioactive $^{35}$S-Cystein and $^{35}$S-Methionine and then treated with either HGF or AntiMET-R for 4 hrs. Media were collected and subjected to immunoprecipitation with an anti-HGFR antibody recognizing the extracellular domain. As shown in FIG. 7A, from culture media of metabolically labelled cells, the inventors immunoprecipitated a band running under non-reducing conditions with an apparent MW of 130 Kd (corresponding to the complex of the extracellular $\alpha\beta$-chains); when the gel was run under reducing condition, the complex was resolved in the two bands of 80 Kd ($\beta$-chain) and 45 Kd ($\alpha$-chain). While HGF stimulation did not enhance this process, receptor shedding was dramatically increased upon antibody binding. According to previous data (15), a slight amount of HGFR ectodomain, is known to be constitutively released in the extra-cellular environment. It is interesting to underline that antibody-induced ectodomain shedding was observed also in cells expressing normal levels of HGFR, such as endothelial cells (FIG. 7B).

By treating cells with increasing amount of antibody for 4 hrs the inventors observed that antibody-mediated HGFR shedding was dose-dependent (FIG. 7C). To analyse the kinetic of antibody-induced HGFR shedding, the inventors stimulated the cells with the same amount of either Anti-MET-R or VSV-G for different times. Increasing levels of the ectodomain were detected in the medium of AntiMET-R— but not VSV-G—treated cells, showing that the observed antibody-induced shedding was specific and time-dependent (FIG. 7D).

Example 6

Antibody-Induced HGFR Shedding Takes Place at the Cell Surface

To test if endocytosis is required for HGFR shedding the inventors utilized a cell line stably transfected with a mutant form of Dynamin (Dyn K44A), which is known to impair clathrin-dependent endocytosis and whose expression is under the control of a tetracycline regulated system. Cells were maintained for 48 hrs either in the presence (Ctr) or in the absence (K44A Dyn) of tetracycline in order to impair endocytosis as a consequence of the expression of mutant Dynamin. As shown in FIG. 7D, antibody-induced shedding was not impaired in cells where clathrin-dependent endocytosis was inhibited.

The proteases more commonly involved in the shedding of membrane proteins belong to the $\alpha$-secretases of the ADAM family. In an attempt to identify the enzyme responsible for HGFR shedding, the Zn-chelating agent 1,10-phenantroline, an inhibitor of the ADAMs and of Zn-dependent proteases, was added to the cells prior to antibody treatment. In this condition, receptor shedding was unaffected (data not shown), showing that the proteolytic cleavage of HGFR ectodomain is not mediated by $\alpha$-secretase but by a Zn-independent protease.

Since it is known that HGFR transcriptionally regulates genes involved in blot clotting, the inventors also checked if a protease of the coagulation system could be responsible for ectodomain shedding. However, the role of procoagulant factors in this process was ruled out since their inhibition with aprotinin did not alter antibody-induced HGFR ectodomain shedding (data not shown). Using a panel of other inhibitors (amiloride, pepstatin A, leupeptin) the inventors also excluded the involvement of other known hydrolases, such as Urokinase, acidic proteases, serine and cystein proteases (data not shown). Moreover, the inventors also proved that shedding of the ectodomain is independent from activation of PKCa, since inhibition of this enzyme with high dose (1 μM) and prolonged treatment (24 hours) with the phorbol ester TPA, did not decrease ectodomain shedding (data not shown).

This set of experiments, all performed with the appropriate positive controls, indicates that the enzyme responsible for HGFR ectodomain shedding is outside the list of the proteases obviously involved in receptor shedding.

Example 7

HGFR Activation is not Required for Antibody-Induced Shedding

As the inventors previously reported, a trimeric complex containing Endophilin, CIN85 and Cbl mediates ligand-dependent down-regulation of HGFR (32). This complex is recruited to the receptor upon HGFR activation and promotes endocytosis, ubiquitinylation and receptor degradation. In order to verify whether receptor activation and signal transduction are required for antibody-induced down-modulation and shedding, the inventors prompted the ability of Anti-MET-R to down-regulate various HGFR mutants. The inventors expressed in COS-7 cells either wild type HGFR or the following mutants: i) MET KD, encoding a "dead" receptor devoid of tyrosine kinase activity, due to a Lys-Ala substitution in the ATP binding pocket, ii) MET "double", encoding a HGFR lacking the tyrosines Y1349, Y1356 docking the signal transducers, iii) MET-GFP, a dominant negative mutant where the sequence encoding the whole intracellular domain of the receptor was replaced by GFP sequences. Forty-eight hours after transfection, cells were treated with AntiMET-R for 3 hrs. Cellular extracts and extracellular media were analysed by Western blot. Unexpectedly, Anti-MET-R was able to trigger down-regulation and to induce HGFR shedding in all the mutants (FIG. 8). This experiment suggests that antibody-induced HGF receptor down-regulation does not require receptor kinase activity, nor the recruitment of cytoplasmic transducers, and that the whole intracellular domain is dispensable for the process. This further confirms that the antibody and the ligand activate different down-regulatory mechanisms.

Example 8

The HGFR Shed Ectodomain Behaves as a "Decoy"

Since it has been shown that a genetically engineered extracellular domain of the HGFR can effectively function as a dominant negative "decoy" molecule (33), the inventors tested the ability of the shed ectodomain in inhibiting HGFR signalling. Cells pretreated for 72 hrs with AntiMET-R or VSV-G were stimulated for different times with HGF either in the presence (FIG. 9, lanes 4-6) or in the absence (lanes 7-9) of HGFR ectodomain in the culture medium. As shown, in the presence of HGFR ectodomain, HGF-triggered Akt phosphorylation was strongly impaired, thus supporting the idea that the shed fragment, like the decoy (33), acts both as a competitor for HGF binding and as a dominant negative molecule interfering with HGFR activation.

Example 9

The Agonist AntiMET-R Antibody DO-24 does not Induce Ectodomain Shedding

The agonist ability of this antibody is not sufficient—per se—to justify its therapeutic activity. In fact, a different anti-MET-R monoclonal antibody (DO-24) that we have examined does not promote shedding of the extracellular portion of the receptor but is able to fully activate the receptor.

Example 10

AntiMET-R Production by Mean of Gene Transfer via Lentiviral Vector

The inventors inserted the AntiMET-R heavy and light chain sequences into a bi-directional lentiviral vector (51) (FIGS. 10A, 15 and 16). This lentiviral vector allows the coordinated expression of two separate cDNAs thanks to the presence of a synthetic promoter (ACCTGGGTT, SEQ ID No.:4) obtained joining a minimal core promoter (minCMV promoter) upstream and in opposite orientation to the hPGK promoter (51). This synthetic promoter is able to drive transcriptional activity in both directions. Thus placing the two cDNAs encoding the AntiMET-R, one upstream in antisense orientation (the light chain) and the other downstream in sense orientation (the heavy chain), is possible to generate coordinately two independent mRNAs. The inventors produced vector particles with transient transfection of 293T cells as described. Then, to permanent modify the genome of target cells, the inventors infected a panel of carcinoma derived cell lines with supernatant containing vector particles. After infection, cells were starved with medium without serum and incubated for 72 hrs to collect cell culture supernatants. AntiMET-R antibody presence was assessed by western Blot analysis (FIG. 10B) and the AntiMET-R quantification was done by ELISA (FIG. 10C). All the transduced cells lines produced the AntiMET-R antibody that was correctly secreted in the culture supernatant. The production of the antibody was variable, in the range 0.2-6 μg/ml, depending on the cell line analysed. The recombinant AntiMET-R specificity was controlled by immunoprecipitation assay (FIG. 11A), while the affinity of binding was assessed by ELISA assay (FIG. 11B). Recombinant AntiMET-R was able to specifically recognize the Met receptor with an affinity in the same range of the one obtained by the AntiMET-R produced conventionally by the hybridoma. Moreover the recombinant AntiMET-R, as the AntiMET-R produced by the hybridoma, was able to induce Met proteolytic cleavage and shedding of the Extra-Cellular Domain (FIG. 12).

Example 11

Transduction with Lentiviral Vector Encoding the AntiMET-R Inhibits the Transformed Phenotype of Cancer Cells In Vitro and In Vivo The inventors transduced HCT-116 cells with lentiviral vector encoding AntiMET-R (25 ng p24/ml). Transduced cells were tested, in comparison with wild-type cells, for their transformed phenotype, analyzing anchorage-independent growth and invasion properties in vitro and in vivo tumorigenesis. For anchorage-independent growth, the inventors seeded cells producing antiMET-R and wild type cells as control in 0.5% agar and the colonies obtained after 15 days of culture were scored. Transduced cells were inhibited in their ability of anchorage-independent growth as they get rise to a reduced number of colonies, smaller in size compared to the colonies generated with wild type cells (FIG. 13A). To test cell invasiveness, the inventors analyzed the ability of cells to invade a reconstituted basement membranes. As shown in FIG. 13B transduced cells showed a reduction of their invasive properties. The inventors tested also the tumorigenesis in vivo of the cells transduced with lentiviral vector encoding the AntiMET-R injecting them sub-cute into the flank of athymic nude mice. Data shown in FIGS. 13 C and D indicated that transduced cells were impaired in their in vivo tumorigenesis properties as tumor lantency and tumor growth were inhibited in comparison to wild type cells.

Example 12

Directed Intra-Tumor Administration of Lentiviral Vector Encoding AntiMET-R Inhibits Tumor Growth To have formal proof of the AntiMET-R gene transfer efficacy, the inventors administrated lentiviral vector particles carrying cDNAs encoding the antibody directly into pre-formed tumors obtained by sub-cute injection of HCT-116 cells into the flak of nude mice. Tumors treated with vectors encoding the AntiMET-R showed slower growth rate in comparison to tumors treated with control vector (FIG. 14).

Example 13

AntiMET-R Binding Site on Met Ectodomain

To map the epitope recognized by Anti-MET-R, immunoprecipitation experiments were performed using different extra cellular domains of the Hepatocyte Growth Factor Receptor (also known as Met ectodomain) (FIG. 17):
  decoy Met (aminoacids 1-932): it is a soluble recombinant protein corresponding to the entire extracellular region of human Met truncated before the transmembrane domain (Michieli et al. 2004);
  SEMA PSI (aminoacids 1-562): it is a truncated form of Decoy Met containing the SEMA domain (aminoacids 1-515) (Stamos et al, 2004; Gherardi et al. 2004) and the PSI region (aminoacids 516-562) (Kozlov et al. 2004).
  PSI IPT (aminoacids 1-24; 516-932): it is a truncated form of Decoy Met containing the endogenous leader sequence (aminoacids 1-24) fused to the PSI region (aminoacids 516-562) and the four IPT domains (aminoacids 563-932) (Bork et al, 1999; Gherardi et al., 2004).
A polihistidine tag and Myc-epitope tag were added at the C-terminus of each molecule.

Decoy Met sequence was derived from the sequence encoded with the Gene Bank Accession Number X54559 (Giordano et al., 1991); this sequence corresponds to the major transcript of the human Met gene that encodes a tyrosine kinase protein that is correctly processed and is located in the membrane.

Other papers refer to the sequence encoded with the Gene Bank Accession Number J02958 (Park ey al., 1987); this numbering corresponds to an alternatively spliced minor transcript containing an insertion of 54 bp in position from nucleotide 2264 to nucleotide 2318. This transcript encodes a tyrosine kinase protein that is not correctly processed and is not located in the membrane (Rodriguez et al., 1991). According to this sequence, the extracellular region of Met corresponds to aminoacids 1-950 and the third IPT domain (IPT3) contains an insertion of 18 aminoacids.

Table 1 summarizes the positions of the different domains of Met according to the sequences X54559 and J02958.

TABLE 1

| MET ectodomains | Gene Bank X54559 (aa-aa) | Gene Bank J02958 (aa-aa) |
| --- | --- | --- |
| Decoy Met | 1-932 | 1-950 |
| SEMA PSI | 1-562 | 1-562 |
| PSI | 1-24; 516-932 | 1-24; 516-950 |
| IPT 1 | 563-656 | 563-656 |
| IPT 2 | 657-741 | 657-741 |
| IPT 3 | 742-838 | 742-856 |
| IPT 4 | 839-932 | 857-950 |

The cDNAs for the engineered molecules were subcloned into the pRRL.sin.PPT.CMV.Wpre lentiviral vector (Follenzi et al., 2000); recombinant lentiviral particles were produced in large scale and used to transduce human tumor cell lines (Michieli et al., 2004).

Conditioned media of MDA-MB-435 cells transduced with myc-tagged Decoy Met, SEMA PSI and PSI IPT were immunoprecipitated with the AntiMET-R antibody and detected by Western blot using a biotinylated anti-myc antibody (FIG. 18, right panel). Equal amounts of conditioned media were loaded as a control for protein expression (FIG. 18, left panel), wherein the control is a conditioned medium of MDA-MB-435 cells transduced with an empty lentiviral vector. As shown in the right panel of FIG. 18, AntiMET-R is able to immunoprecipitate Decoy Met and PSI-IPT but not SEMA-PSI. Therefore, it recognized an epitope in the IPT region.

To map more in detail the epitope recognized by the antibody AntiMET-R immunoprecipitation experiments were performed using single IPT domains (Bork et al., 1999). Each IPT is a truncated form of PSI-IPT containing the endogenous leader sequence (aminoacids 1-24) fused to IPT 1 (aminoacids 563-656) or IPT 2 (aminoacids 657-741) or IPT 3 (aminoacids 742-838) or IPT 4 (aminoacids 839-932).

A polihistidine tag and Flag-epitope tag were added to the C-terminus of each molecule. The cDNAs for the engineered molecules were subcloned into the same lentiviral vector as previously reported and recombinant lentiviral particles were used to transduce human tumor cell lines.

All these recombinant proteins are soluble factors, but IPT 2 is not secreted into the conditioned medium of the transduced cells. For this reason the immunoprecipitation experiments were performed on cell lysates.

Cell lysates of MDA-MB-435 cells transduced with flag-tagged single IPTs were immunoprecipitated with the Anti-MET-R antibody and detected by Western blot using an anti-flag antibody (FIG. 19, left panel); similar amounts of cell lysates were immunoprecipitated with an anti-flag antibody and detected by Western blot using the same anti-flag antibody, as a control for protein expression (FIG. 19, right panel).

As shown in the left panel, AntiMET-R is able to immunoprecipitate IPT 4, but none of the other three IPT domains. AntiMET-R recognizes an epitope contained in the IPT 4 domain of MET extracellular region.

Example 14

AntiMET-R Recognized the HGFR in Intact Cells Both by FACS Analysis or Immunofluorescence Analysis GTL-16 cells, a human gastric carcinoma cell line, were incubated with the AntiMET-R antibody. Profile of GTL-16 analysed by flow cytometry revealed that the antiMET-R was able to specifically stain cells expressing the HGFR. Infact the mean of fluorescence intensity in cells labelled with the antiMet-R antibody was increased respect to ctrl cells (FIG. 20, panel A). GTL-16 cells were also incubated, after fixation, with the antiMet-R antibody to perform an immunofluoresce analysis. The staining revealed a specific labelling on the cell surfaces corresponding to the Met receptor (FIG. 20, panels B, C).

Naturally, while the principle of the invention remains the same, the details of construction and the embodiments may widely vary with respect to what has been described and illustrated purely by way of example, without departing from the scope of the present invention as defined in the appended claims.

BIBLIOGRAPHY

1. Hudson, P. J. (1999) *Curr. Opin. Immunol.* 11, 548-557.
2. Hudson, P. J. & Souriau, C. (2003) *Nat. Med.* 9, 129-134.
3. Gschwind, A., Fischer, O. M. & Ullrich, A. (2004) *Nat. Rev. Cancer* 4, 361-370.
4. Cragg, M. S., French, R. R. & Glennie, M. J. (1999) *Curr. Opin. Immunol.* 11, 541-547.
5. Ferrara, N., Hillan, K. J., Gerber, H. P. & Novotny, W. (2004) *Nat. Rev. Drug Discov.* 3, 391-400.
6. Li, S., Schmitz, K. R., Jeffrey, P. D., Wiltzius, J. J., Kussie, P. & Ferguson, K. M. (2005) *Cancer Cell* 7, 301-311.
7. Hynes, N. E. & Lane, H. A. (2005) *Nat. Rev. Cancer* 5, 341-354.
8. Trusolino, L. & Comoglio, P. M. (2002) *Nat. Rev. Cancer* 2, 289-300.
9. Schmidt, L., Duh, F. M., Chen, F., Kishida, T., Glenn, G., Choyke, P., Scherer, S. W., Zhuang, Z., Lubensky, I., Dean, M. et al. (1997) *Nat. Genet.* 16, 68-73.
10. Kim, I. J., Park, J. H., Kang, H. C., Shin, Y., Lim, S. B., Ku, J. L., Yang, H. K., Lee, K. U. & Park, J. G. (2003) *J. Med. Genet.* 40, e97.
11. Di Renzo, M. F., Olivero, M., Giacomini, A., Porte, H., Chastre, E., Mirossay, L., Nordlinger, B., Bretti, S., Bottardi, S., Giordano, S. et al. (1995) *Clin. Cancer Res.* 1, 147-154.
12. Corso, S., Comoglio, P. M. & Giordano, S. (2005) *Trends Mol. Med.* 11, 284-292.
13. Comoglio, P. M. & Trusolino, L. (2002) *J. Clin. Invest* 109, 857-862.
14. Maulik, G., Shrikhande, A., Kijima, T., Ma, P. C., Morrison, P. T. & Salgia, R. (2002) *Cytokine Growth Factor Rev.* 13, 41-59.
15. Birchmeier, C., Birchmeier, W., Gherardi, E. & Vande Woude, G. F. (2003) *Nat. Rev. Mol. Cell. Biol.* 4, 915-925.
16. Kong-Beltran, M., Stamos, J. & Wickramasinghe, D. (2004) *Cancer Cell* 6, 75-84.
17. Ivan, M., Bond, J. A., Prat, M., Comoglio, P. M. & Wynford-Thomas, D. (1997) *Oncogene* 14, 2417-2423.
18. Gambarotta, G., Boccaccio, C., Giordano, S., Ando, M., Stella, M. C. & Comoglio, P. M. (1996) *Oncogene* 13, 1911-1917.
19. Pennacchietti, S., Michieli, P., Galluzzo, M., Mazzone, M., Giordano, S. & Comoglio, P. M. (2003) *Cancer Cell* 3, 347-361.
20. Prat, M., Crepaldi, T., Pennacchietti, S., Bussolino, F. & Comoglio, P. M. (1998) *J. Cell Sci.* 111 Pt 2), 237-247.
21. Giordano S, Maffe A, Williams T A, Artigiani S, Gual P, Bardelli A, Basilico C. Michieli, P., Comoglio P M. (2000), FASEB J., 2, 399-406.
22. Boccaccio C., Ando' M., Comoglio P M., (2002) FASEB J 1, 120-2.
23. Folkman, J. (1971) *N. Engl. J. Med.* 285, 1182-1186.
24. Bussolino, F., Di Renzo, M. F., Ziche, M., Bocchietto, E., Olivero, M., Naldini, L., Gaudino, G., Tamagnone, L., Coffer, A. & Comoglio, P. M. (1992) *J. Cell Biol.* 119, 629-641.
25. Clark M. (2000) *Imm. Today* 21 397-402.
26. Prat, M., Crepaldi, T., Gandino, L., Giordano, S., Longati, P. & Comoglio, P. (1991) *Mol. Cell. Biol.* 11, 5954-5962.
27. Giordano, S., Ponzetto, C., Di Renzo, M. F., Cooper, C. S. & Comoglio, P. M. (1989) *Nature* 339, 155-156.
28. Frisch, S. M. & Francis, H. (1994) *J. Cell Biol.* 124, 619-626.
29. Trusolino, L., Bertotti, A. & Comoglio, P. M. (2001) *Cell* 107, 643-654.
30. Di Fiore, P. P. & De Camilli, P. (2001) *Cell* 106, 1-4
31. Arribas, J. & Borroto, A. (2002) *Chem. Rev.* 102, 4627-4638.
32. Petrelli, A., Gilestro, G. F., Lanzardo, S., Comoglio, P. M., Migone, N. & Giordano, S. (2002) *Nature* 416, 187-190.
33. Michieli, P., Mazzone, M., Basilico, C., Cavassa, S., Sottile, A., Naldini, L. & Comoglio, P. M. (2004) *Cancer Cell* 6, 61-73.
34. Christensen J G, Schreck R, Burrows J, Kuruganti P, Chan E, Le P, Chen J, Wang X, Ruslim L, Blake R, Lipson K E, Ramphal J, Do S, Cui J J, Chemington J M, Mendel D B. (2003) *Cancer Res.* November 1; 63(21):7345-55.
35. Berthou S, Aebersold D M, Schmidt L S, Stroka D, Heigl C, Streit B, Stalder D, Gruber G, Liang C, Howlett A R, Candinas D, Greiner R H, Lipson K E, Zimmer Y. (2004) *Oncogene* July 8; 23(31):5387-93.
36. Morotti A, Mila S, Accornero P, Tagliabue E, Ponzetto C. (2002) *Oncogene* July 25; 21 (32):4885-93.
37. Sattler M, Pride Y B, Ma P, Gramlich J L, Chu S C, Quinnan L A, Shirazian S, Liang C, Podar K, Christensen J G, Salgia R. (2003) *Cancer Res.* September 1; 63(17):5462-9.
38. Wang X, Le P, Liang C, Chan J, Kiewlich D, Miller T, Harris D, Sun L, Rice A, Vasile S, Blake R A, Howlett A R, Patel N, McMahon G, Lipson K E. (2003) *Mol Cancer Ther.* November; 2(11):1085-92.
39. Stamos J, Lazarus R A, Yao X, Kirchhofer D, Wiesmann C, (2004) EMBO J; 23:2325-2335.
40. Gherardi E, Love C A, Esnouf R M, Jones E Y, (2004) *Curr. Opin. Struct. Biol.,* 14: 669-678.
41. Kozlov G, Perreault A, Schrag J D, Park M, Cygler M, Gehring K, Ekiel I, (2004) *Biochem Biophys Res Commun.;* 321(1):234-40.
42. Bork P, Doerks T, Springer T A, Snel B, (1999) *Trends Biochem Sci.;* 24(7):261-3.
43. Giordano S, Ponzetto C, Comoglio P M, (1991) *J. Biol. Chem.;* 266:19558-19564.
44. Park M, Dean M, Kaul K, Braun M J, Gonda M A, Vande Woude G, (1987) *PNAS;* 84:6379-6383.
45. Rodrigues G A, Naujokas M A, Prak M, (1991) *Mol. Cell Biol.;* 11:2962-2970.
46. Follenzi A, Ailles L E, Bakovic S, Geuna M, Naldini L, (2000) *Nat. Genet.;* 25:217-222.
47. Schaeffer W. I., and Friend K (1976) *Cancer lett.;* 1: 259-262.
48. Senguptas, Gherardi E, sellers L A, Wood J M, Sasisekharan R, Fan T P (2003). *Arterioscler Thromb Vasc Biol.* 23:69-75
49. Worden B, Yang X P, Lee T L, Bagain L, Yeh N T, Cohen J G, Van Waes C, Chen Z. (2005) *Cancer Res.;* 65:7071-80.
50. Zhang Y W, Su Y, Volpert O V, Vande Woude G F. (2003) *Proc Natl Acad Sci USA.;* 100:12718-23.
51. Amendola M, Venneri M A, Biffi A, Vigna E, Naldini L. (2005) *Nature Biotech.* 23: 108-116.

The invention claimed is:

1. A method of treating a tumor or tumor metastases comprising administering to a patient in need thereof:
   i) the anti-Met monoclonal antibody AntiMET-R,
   ii) a fragment containing the epitope binding region of the anti-Met monoclonal antibody AntiMET-R or
   iii) a genetically engineered antibody containing the complementarity determining regions (CDRs) of the anti-Met monoclonal antibody AntiMET-R, wherein CDR-H1 is SEQ ID NO.:8, CDR-H2 is SEQ ID NO.:9, CDR-H3 is SEQ ID NO.:10, CDR-L1 is SEQ ID NO.:11, CDR-L2 is SEQ ID NO.:12 and CDR-L3 is SEQ ID NO.:13
   in an amount sufficient to effect said treatment, wherein said antibody AntiMET-R is produced by the hybridoma cell line ICLC PD 05006.

2. The method according to claim 1, wherein said antibody, said fragment or said genetically engineered antibody is in the form of soluble protein.

3. The method according to claim 1, wherein said antibody or said genetically engineered antibody is produced by a method selected from the group consisting of DNA recombinant technique, solid phase synthesis, and liquid phase synthesis.

4. The method according to claim 1, wherein said fragment is selected from the group consisting of Fab, F(ab')$_2$, Fab', Fv, scFv, and a peptide containing the epitope binding region.

5. The method according to claim 1, wherein said fragment is produced by a method selected from the group consisting of proteolytic cleavage of said antibody, DNA recombinant technique, solid phase synthesis, and liquid phase synthesis.

6. The method according to claim 1, wherein said administration is by injection or by infusion.

7. The method according to claim 1, wherein said tumor is a colorectal tumor or a liver tumor.

8. The method according to claim 1 wherein said method further comprises administering to said patient at least one kinase inhibitor.

9. The method according to claim 8 wherein said at least one kinase inhibitor is selected from the group consisting of K252A staurosporin analogue; (3Z)-5-[(2,6-dichlorobenzyl)sulfonyl]-3-[(3,5-dimethyl-4-{[(2R)-2-(pyrrolidin-1-ylmethy)pyrrolidin-1-yl]carbonyl}-1H-pyrrol-2-yl)methylene]-1,3-dihydro-2H-indol-2-one;[(3Z)-N-(3-chlorophenyl)-3-({3,5-dimethyl-4-[(4-methylpiperazin-1-yl)carbonyl]-1H-pyrrol-2-yl{methylene)-N-methyl-2-oxoindoline-5-sulfonamide};[(3Z)-5-(2,3-dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H -indol-2- one]; and [(3Z)-N-(3-chlorophenyl)-3-{[3,5-dimethyl-4-(3-morpholin-4-ylpropyl)-1H-pyrrol-2-yl]methylene]}-N-methyl-2-oxoindoline-5-sulfonamide].

10. The method according to claim 9 wherein said at least one kinase inhibitor is administered in combination with said antibody, said fragment or said genetically engineered antibody.

11. The method according to claim 9 wherein said at least one kinase inhibitor is administered separately from said antibody, said fragment or said genetically engineered antibody.

12. The method according to claim 9 wherein said at least one kinase inhibitor is administered simultaneously with said antibody, said fragment or said genetically engineered antibody.

13. The method according to claim 9 wherein said at least one kinase inhibitor and said antibody, said fragment or said genetically engineered antibody are administered sequentially.

* * * * *

SEQUENCE LISTING

<160> NUMBER OF SEQ ID NOS: 13

<210> SEQ ID NO 1
<211> LENGTH: 1386
<212> TYPE: DNA
<213> ORGANISM: artificial
<220> FEATURE:
<223> OTHER INFORMATION: AntiMET-R heavy chain

<400> SEQUENCE: 1

| | | | | | |
|---|---|---|---|---|---|
| atgggatgga | gctatatcat | cctcttttg | gtagcaacag | ctacagatgg | ccactcccag | 60 |
| gtccaactgc | agcagcctgg | gactgaactg | gtgaagcctg | ggcttcagt | gaagctgtcc | 120 |
| tgcaaggctt | ctggctacac | cttcaccagt | tactggatac | actgggtgaa | gcagaggcct | 180 |
| ggacaaggcc | ttgagtggat | tggagagatt | aatcctagca | gcggtcgtac | taactacaac | 240 |
| gagaaattca | gaacaaggt | cacagtgact | gtagacaaat | cttccaccac | agcctacatg | 300 |
| caactcagca | acctgacatc | tgaggactct | gcggtctatt | actgtgcaag | tagggctac | 360 |
| tggggccaag | gcaccactct | cacagtctcc | tcagccaaaa | caacagcccc | atcggtctat | 420 |
| ccactggccc | ctgtgtgtgg | aaatacaact | ggctcctcgg | tgactctagg | atgcctggtc | 480 |
| aagggttatt | tccctgagcc | agtgaccttg | acctggaact | ctggatccct | gtccagtggt | 540 |
| gtgcacacct | tcccagctgt | cctgcagtct | gacctctaca | ccctcagcag | ctcagtgact | 600 |
| gtaacctcga | gcacctggcc | cagccagtcc | atcacctgca | atgtggccca | cccggcaagc | 660 |
| agcaccaagg | tggacaagaa | aattgagccc | agagggccca | caatcaagcc | ctgtcctcca | 720 |
| tgcaaatgcc | cagcacctaa | cctcttgggt | ggaccatccg | tcttcatctt | ccctccaaag | 780 |
| atcaaggatg | tactcatgat | ctccctgagc | cccatagtca | catgtgtggt | ggtggatgtg | 840 |
| agcgaggatg | acccagatgt | ccagatcagc | tggtttgtga | acaacgtgga | agtacacaca | 900 |
| gctcagacac | aaacccatag | agaggattac | aacagtactc | tccgggtggt | cagtgccctc | 960 |
| cccatccagc | accaggactg | gatgagtggc | aaggagttca | atgcaaggt | caacaacaaa | 1020 |
| gacctcccag | cgcccatcga | gagaaccatc | tcaaaaccca | aagggtcagt | aagagctcca | 1080 |
| caggtatatg | tcttgcctcc | accagaagaa | gagatgacta | agaaacaggt | cactctgacc | 1140 |
| tgcatggtca | cagacttcat | gcctgaagac | atttacgtgg | agtggaccaa | caacgggaaa | 1200 |
| acagagctaa | actacaagaa | cactgaacca | gtcctggact | ctgatggttc | ttacttcatg | 1260 |
| tacagcaagc | tgagagtgga | aaagaagaac | tgggtggaaa | gaatagcta | ctcctgttca | 1320 |
| gtggtccacg | agggtctgca | aatcaccac | acgactaaga | gcttctcccg | gactccgggt | 1380 |
| aaatga | | | | | 1386 |

<210> SEQ ID NO 2
<211> LENGTH: 717
<212> TYPE: DNA
<213> ORGANISM: artificial
<220> FEATURE:
<223> OTHER INFORMATION: AntiMET-R light chain

<400> SEQUENCE: 2

| | | | | | |
|---|---|---|---|---|---|
| atggagacag | acacaatcct | gctatgggtg | ctgctgctct | gggttccagg | ctccactggt | 60 |
| gacattgtgc | tgacccaatc | tccagcttct | ttggctgtgt | ctctagggca | gagggccacc | 120 |
| atctcctgca | aggccagcca | aagtgttgat | tatgatggtg | atagttatat | gagttggttc | 180 |
| caacagagac | caggacagcc | acccaaactc | ctcatctctg | ctgcatccaa | tctagaatct | 240 |

```
gggatcccag ccaggtttag tggcagtggc tctgggacag acttcaccct caatatccat      300
cctgtggagg aggaggatgt tgcaacctat tactgtcagc aaagttatga ggatccgctc      360
acgttcggtg ctgggaccaa gctggagctg aaacgggctg atgctgcacc aactgtatcc      420
atcttcccac catccagtga gcagttaaca tctggaggtg cctcagtcgt gtgcttcttg      480
aacaacttct accccaaaga catcaatgtc aagtggaaga ttgatggcag tgaacgacaa      540
aatggcgtcc tgaacagttg gactgatcag gacagcaaag acagcaccta cagcatgagc      600
agcaccctca cgttgaccaa ggacgagtat gaacgacata cagctatac ctgtgaggcc       660 actcacaaga catctacttc acccattgtc aagagcttca acaggaatga gtgttag        717
```

```
<210> SEQ ID NO 3
<211> LENGTH: 1473
<212> TYPE: DNA
<213> ORGANISM: artificial
<220> FEATURE:
<223> OTHER INFORMATION: Anti-MET-R Heavy chain with a tag sequence to
      the 3'

<400> SEQUENCE: 3
```

```
atgggatgga gctatatcat cctcttttg gtagcaacag ctacagatgg ccactcccag       60
gtccaactgc agcagcctgg gactgaactg gtgaagcctg ggcttcagt gaagctgtcc       120 tgcaaggctt ctggctacac cttcaccagt tactggatac actgggtgaa gcagaggcct     180
ggacaaggcc ttgagtggat tggagagatt aatcctagca gcggtcgtac taactacaac     240
gagaaattca gaacaaggt cacagtgact gtagacaaat cttccaccac agcctacatg      300
caactcagca acctgacatc tgaggactct gcggtctatt actgtgcaag tagggggctac    360 tggggccaag gcaccactct cacagtctcc tcagccaaaa caacagcccc atcggtctat     420
ccactggccc ctgtgtgtgg aaatacaact ggctcctcgg tgactctagg atgcctggtc     480
aagggttatt tccctgagcc agtgaccttg acctggaact ctggatccct gtccagtggt    540
gtgcacacct tcccagctgt cctgcagtct gacctctaca ccctcagcag ctcagtgact     600
gtaacctcga gcacctggcc cagccagtcc atcacctgca atgtggccca cccggcaagc    660
agcaccaagg tggacaagaa aattgagccc agagggccca caatcaagcc ctgtcctcca    720
tgcaaatgcc cagcacctaa cctcttgggt ggaccatccg tcttcatctt ccctccaaag    780
atcaaggatg tactcatgat ctccctgagc cccatagtca catgtgtggt ggtggatgtg    840
agcgaggatg acccagatgt ccagatcagc tggtttgtga acaacgtgga agtacacaca     900
gctcagacac aaacccatag agaggattac aacagtactc tccgggtggt cagtgccctc    960
cccatccagc accaggactg gatgagtggc aaggagttca atgcaaggt caacaacaaa     1020 gacctcccag cgcccatcga gagaaccatc tcaaaaccca aagggtcagt aagagctcca   1080
caggtatatg tcttgcctcc accagaagaa gagatgacta gaaacaggt cactctgacc      1140 tgcatggtca cagacttcat gcctgaagac atttacgtgg agtggaccaa caacgggaaa    1200
acagagctaa actacaagaa cactgaacca gtcctggact ctgatggttc ttacttcatg    1260
tacagcaagc tgagagtgga aaagaagaac tgggtggaaa gaaatagcta ctcctgttca    1320
gtggtccacg agggtctgca caatcaccac acgactaaga gcttctcccg gactccgggt    1380
aaagctagct ctgactacaa ggacgacgat gacaagagcg attacaaaga cgatgatgat    1440
aagctgcagc atcaccacca tcatcaccat tga                                  1473
```

```
<210> SEQ ID NO 4
<211> LENGTH: 9
```

-continued

```
<212> TYPE: DNA
<213> ORGANISM: artificial
<220> FEATURE:
<223> OTHER INFORMATION: synthetic promoter - upstream

<400> SEQUENCE: 4 acctgggtt                                                              9

<210> SEQ ID NO 5
<211> LENGTH: 13
<212> TYPE: DNA
<213> ORGANISM: artificial
<220> FEATURE:
<223> OTHER INFORMATION: synthetic promoter - downstream

<400> SEQUENCE: 5
attggttggt tgg                                                        13

<210> SEQ ID NO 6
<211> LENGTH: 461
<212> TYPE: PRT
<213> ORGANISM: artificial
<220> FEATURE:
<223> OTHER INFORMATION: AntiMET-R heavy chain

<400> SEQUENCE: 6

Met Gly Trp Ser Tyr Ile Ile Leu Phe Leu Val Ala Thr Ala Thr Asp
 1               5                  10                  15

Gly His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Lys Gln Arg Pro Gly Gln Gly Leu
    50                  55                  60

Glu Trp Ile Gly Glu Ile Asn Pro Ser Ser Gly Arg Thr Asn Tyr Asn
65                  70                  75                  80

Glu Lys Phe Lys Asn Lys Val Thr Val Thr Val Asp Lys Ser Ser Thr
                85                  90                  95

Thr Ala Tyr Met Gln Leu Ser Asn Leu Thr Ser Glu Asp Ser Ala Val
            100                 105                 110

Tyr Tyr Cys Ala Ser Arg Gly Tyr Trp Gly Gln Gly Thr Thr Leu Thr
        115                 120                 125

Val Ser Ser Ala Lys Thr Thr Ala Pro Ser Val Tyr Pro Leu Ala Pro
    130                 135                 140

Val Cys Gly Asn Thr Thr Gly Ser Ser Val Thr Leu Gly Cys Leu Val
145                 150                 155                 160

Lys Gly Tyr Phe Pro Glu Pro Val Thr Leu Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Thr Ser Ser Thr Trp Pro Ser
        195                 200                 205

Gln Ser Ile Thr Cys Asn Val Ala His Pro Ala Ser Ser Thr Lys Val
    210                 215                 220

Asp Lys Lys Ile Glu Pro Arg Gly Pro Thr Ile Lys Pro Cys Pro Pro
225                 230                 235                 240

Cys Lys Cys Pro Ala Pro Asn Leu Leu Gly Gly Pro Ser Val Phe Ile
                245                 250                 255

Phe Pro Pro Lys Ile Lys Asp Val Leu Met Ile Ser Leu Ser Pro Ile
```

```
                    260                 265                 270
Val Thr Cys Val Val Asp Val Ser Glu Asp Pro Asp Val Gln
            275                 280                 285

Ile Ser Trp Phe Val Asn Asn Val Glu Val His Thr Ala Gln Thr Gln
            290                 295                 300

Thr His Arg Glu Asp Tyr Asn Ser Thr Leu Arg Val Val Ser Ala Leu
305                 310                 315                 320

Pro Ile Gln His Gln Asp Trp Met Ser Gly Lys Glu Phe Lys Cys Lys
                    325                 330                 335

Val Asn Asn Lys Asp Leu Pro Ala Pro Ile Glu Arg Thr Ile Ser Lys
            340                 345                 350

Pro Lys Gly Ser Val Arg Ala Pro Gln Val Tyr Val Leu Pro Pro Pro
            355                 360                 365

Glu Glu Glu Met Thr Lys Lys Gln Val Thr Leu Thr Cys Met Val Thr
            370                 375                 380

Asp Phe Met Pro Glu Asp Ile Tyr Val Glu Trp Thr Asn Asn Gly Lys
385                 390                 395                 400

Thr Glu Leu Asn Tyr Lys Asn Thr Glu Pro Val Leu Asp Ser Asp Gly
                    405                 410                 415

Ser Tyr Phe Met Tyr Ser Lys Leu Arg Val Glu Lys Lys Asn Trp Val
                    420                 425                 430

Glu Arg Asn Ser Tyr Ser Cys Ser Val Val His Glu Gly Leu His Asn
            435                 440                 445

His His Thr Thr Lys Ser Phe Ser Arg Thr Pro Gly Lys
            450                 455                 460

<210> SEQ ID NO 7
<211> LENGTH: 238
<212> TYPE: PRT
<213> ORGANISM: artificial
<220> FEATURE:
<223> OTHER INFORMATION: AntiMET-R light chain

<400> SEQUENCE: 7

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
            35                  40                  45

Val Asp Tyr Asp Gly Gly Ser Tyr Met Ser Trp Phe Gln Gln Arg Pro
50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
                100                 105                 110

Gln Gln Ser Tyr Glu Asp Pro Leu Thr Phe Gly Ala Gly Thr Lys Leu
            115                 120                 125

Glu Leu Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175
```

Ser Glu Arg Gln Asn Gly Val Leu Asn Ser Trp Thr Asp Gln Asp Ser
         180                 185                 190

Lys Asp Ser Thr Tyr Ser Met Ser Ser Thr Leu Thr Leu Thr Lys Asp
         195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 8
<211> LENGTH: 8
<212> TYPE: PRT
<213> ORGANISM: artificial
<220> FEATURE:
<223> OTHER INFORMATION: AntiMET-R heavy chain - CDR-H1

<400> SEQUENCE: 8

Gly Tyr Thr Phe Thr Ser Tyr Trp
1               5

<210> SEQ ID NO 9
<211> LENGTH: 8
<212> TYPE: PRT
<213> ORGANISM: artificial
<220> FEATURE:
<223> OTHER INFORMATION: AntiMET-R heavy chain - CDR-H2

<400> SEQUENCE: 9

Ile Asn Pro Ser Ser Gly Arg Thr
1               5

<210> SEQ ID NO 10
<211> LENGTH: 5
<212> TYPE: PRT
<213> ORGANISM: artificial
<220> FEATURE:
<223> OTHER INFORMATION: Anti-MET-R heavy chain - CDR-H3

<400> SEQUENCE: 10

Ala Ser Arg Gly Tyr
1               5

<210> SEQ ID NO 11
<211> LENGTH: 10
<212> TYPE: PRT
<213> ORGANISM: artificial
<220> FEATURE:
<223> OTHER INFORMATION: AntiMET-R light chain - CDR-L1

<400> SEQUENCE: 11

Gln Ser Val Asp Tyr Asp Gly Gly Ser Tyr
1               5                   10

<210> SEQ ID NO 12
<211> LENGTH: 3
<212> TYPE: PRT
<213> ORGANISM: artificial
<220> FEATURE:
<223> OTHER INFORMATION: AntiMET-R light chain - CDR-L2

<400> SEQUENCE: 12

Ala Ala Ser
1

<210> SEQ ID NO 13

```
<211> LENGTH: 9
<212> TYPE: PRT
<213> ORGANISM: artificial
<220> FEATURE:
<223> OTHER INFORMATION: AntiMET-R light chain - CDR-L3

<400> SEQUENCE: 13

Gln Gln Ser Tyr Glu Asp Pro Leu Thr
1               5
```